US012387843B2

(12) United States Patent
Bhimavarapu et al.

(10) Patent No.: US 12,387,843 B2
(45) Date of Patent: Aug. 12, 2025

(54) PATIENT SUPPORT APPARATUS AND HEADWALL UNIT SYNCING

(71) Applicant: Stryker Corporation, Kalamazoo, MI (US)

(72) Inventors: Krishna Sandeep Bhimavarapu, Kalamazoo, MI (US); Alexander Josef Bodurka, Portage, MI (US); Jerald A. Trepanier, Augusta, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/561,457

(22) PCT Filed: May 24, 2022

(86) PCT No.: PCT/US2022/030707
§ 371 (c)(1),
(2) Date: Nov. 16, 2023

(87) PCT Pub. No.: WO2022/251200
PCT Pub. Date: Dec. 1, 2022

(65) Prior Publication Data
US 2024/0249835 A1  Jul. 25, 2024

Related U.S. Application Data

(60) Provisional application No. 63/193,778, filed on May 27, 2021.

(51) Int. Cl.
*G16H 40/67* (2018.01)
*G08C 17/02* (2006.01)
*H04L 67/12* (2022.01)

(52) U.S. Cl.
CPC ............. *G16H 40/67* (2018.01); *G08C 17/02* (2013.01); *H04L 67/12* (2013.01)

(58) Field of Classification Search
CPC .......... G08B 7/06; G08C 17/02; G16H 40/67; G16H 40/20; G16H 40/63; H04L 67/12;
(Continued)

(56) References Cited

U.S. PATENT DOCUMENTS 5,335,313 A  8/1994 Douglas
7,852,208 B2  12/2010 Collins, Jr. et al.
(Continued)

FOREIGN PATENT DOCUMENTS

WO  9427544 A2  5/1994
WO  2021236437 A1  11/2021

*Primary Examiner* — Adnan Aziz
(74) *Attorney, Agent, or Firm* — Warner Norcross + Judd LLP

(57) ABSTRACT

A wireless communication system for exchanging messages between a patient support apparatus and a headwall unit includes a syncing function wherein certain settings that are present in the headwall unit before a communication link is established with the patient support apparatus are synced with values for those settings that come from the patient support apparatus after the communication link is initially established. Similarly, certain settings that are present in the patient support apparatus before the communication link is established are synced with values for those settings that come from the headwall unit after the communication link is initially established. The syncing function thereby ensures that, upon the initial establishment of the communication link, the patient support apparatus settings will match the headwall settings, and vice versa.

20 Claims, 9 Drawing Sheets

(58) Field of Classification Search
CPC . A61G 7/05; A61G 7/015; A61G 7/00; A61G 7/0506
See application file for complete search history.

(56) References Cited

U.S. PATENT DOCUMENTS

| | | |
|---|---|---|
| 9,999,375 B2 | 6/2018 | Hayes et al. |
| 10,235,845 B2 | 3/2019 | Bhimavarapu et al. |
| 10,257,063 B2 | 4/2019 | Bhimavarapu et al. |
| 2002/0167417 A1 | 11/2002 | Welles, II et al. |
| 2014/0043150 A1 | 2/2014 | Wagner et al. |
| 2016/0038361 A1 | 2/2016 | Bhimavarapu et al. |
| 2018/0293849 A1* | 10/2018 | Bhimavarapu ...... A61B 5/7475 |
| 2018/0296415 A1* | 10/2018 | Seim .................... A61G 7/0524 |
| 2018/0344254 A1 | 12/2018 | George et al. |
| 2019/0008709 A1 | 1/2019 | Bhimavarapu et al. |
| 2019/0046379 A1 | 2/2019 | Constant et al. |
| 2019/0150737 A1 | 5/2019 | Bodurka et al. |
| 2019/0183705 A1* | 6/2019 | Bodurka .................. H04B 5/72 |
| 2019/0188992 A1 | 6/2019 | Bodurka et al. |
| 2020/0050750 A1* | 2/2020 | Heil ....................... G16H 10/60 |
| 2020/0101303 A1* | 4/2020 | Hayes ................. A61N 1/37282 |
| 2020/0327784 A1 | 10/2020 | Bodurka et al. |

\* cited by examiner

| | CONDITION | SYNC DIRECTION | STATE VALUES |
|---|---|---|---|
| 152a | READING_LIGHT_KEY, | Bed_To_Wall | ON/OFF |
| 152b | ROOM_LIGHT_KEY, | Bed_To_Wall | ON/OFF |
| 152c | NURSE_ANSWER_LT_P_KEY, | Wall_To_Bed | ON/OFF |
| 152d | NURSE_CALL_LT_P_KEY, | Wall_To_Bed | ON/OFF |
| 152e | NURSE_CALL_P_KEY | Bed_To_Wall | ON/OFF |
| 152f | PRIORITY_KEY, | Bed_To_Wall | ON/OFF |
| 152g | TV_P_KEY, | Bed_To_Wall | ON/OFF |
| 152h | TV_TYPE_WALL_TO_BED_KEY, | Wall_To_Bed | TV Brand/type |
| 152i | NC_INTLK_WALL_TO_BED_KEY, | Wall_To_Bed | ON/OFF |
| 152j | STD_INTLK_WALL_TO_BED_KEY, | Wall_To_Bed | ON/OFF |
| 152k | AUDIO_INTLK_WALL_TO_BED_KEY, | Wall_To_Bed | ON/OFF |
| 152l | FORCE_INTLK_WALL_TO_BED_KEY, | Wall_To_Bed | ON/OFF |
| 152m | DISABLE_CABLE_DETECTION_WALL_TO_BED_KEY, | Wall_To_Bed | Enabled/Disabled |
| 152n | VOL_MODE_WALL_TO_BED_KEY, | Wall_To_Bed | Amplification Level |
| 152o | NC_MODE_WALL_TO_BED_KEY, | Wall_To_Bed | NC type |
| 152p | HEADWALL_VOLTAGE_WALL_TO_BED_KEY, | Wall_To_Bed | Hi, Med, Lo, etc. |
| 152q | WALL_CABLE_CONNECTED_KEY, | Wall_To_Bed | Connected/Disconnected |
| 152r | WALL_CONFIGURED_KEY, | Wall_To_Bed | Yes/No |
| 152s | WALL_DIAGNOSTICS_REQUEST, | Bed_To_Wall | Yes/No |
| 152t | PIN_SYNC_DONE_WALL_KEY, | Wall_To_Bed | Yes/No |
| 152u | WALL_BATTERY_STATUS_KEY, | Wall_To_Bed | Charge % |
| 152v | SET_IR_SESSION_ID, | Bed_To_Wall | Session ID |

FIG. 8

Pin 1   Bed Monitoring Status On
Pin 2   Read Light
Pin 3   Room Light
Pin 4   Speaker High
Pin 5   Potentiometer Wiper
Pin 6   Bed Exit Status On
Pin 7   Nurse Call Interlock
Pin 8   Audio Transfer -
Pin 9   Audio Transfer +
Pin 10 Interlock +
Pin 11 Interlock -
Pin 12 Bed Monitoring Fowler 30 deg. Alert
Pin 13 No Connect
Pin 14 Potentiometer Low Common
Pin 15 Potentiometer High Common (Std.) / Audio (STV)
Pin 16 Nurse Answer Light +
Pin 17 Bed Monitor Alert
Pin 18 Bed Monitoring Siderail Alert
Pin 19 Nurse Call Light +
Pin 20 No Connect
Pin 21 No Connect
Pin 22 No Connect
Pin 23 Brake Status On
Pin 24 No Connect
Pin 25 Nurse Call +
Pin 26 Nurse Call NO/NC
Pin 27 Room/Read Light Common
Pin 28 Nurse Call Light -
Pin 29 Nurse Answer Light -
Pin 30 Priority NO/NC
Pin 31 Priority Common
Pin 32 Bed Monitoring Low Height Alert
Pin 33 TV - (Std.) / Data (STV)
Pin 34 TV + (Std.) / Common (STV)
Pin 35 Speaker Low Common
Pin 36 Audio Shield
Pin 37 Bed Monitoring Common FIG. 11
(Prior Art)

PATIENT SUPPORT APPARATUS AND HEADWALL UNIT SYNCING

CROSS REFERENCE TO RELATED APPLICATIONS

The application claims priority to and all advantages of U.S. Provisional Patent Application No. 63/193,778 filed on 27 May 2022, the content of which is incorporated herein by reference.

BACKGROUND

The present disclosure relates to patient support apparatuses, such as beds, cots, stretchers, recliners, or the like, that are adapted to communicate with an existing nurse call system and/or one or more room devices.

Existing hospital beds often communicate with a nurse call system over a communication link. In some situations where the communication link is a wireless communication link, the hospital bed may communicate with a headwall unit attached to a headwall of a healthcare facility room. The headwall unit acts as an intermediary device between the bed and a wall outlet of the nurse call system. The headwall unit therefore forwards communications received from the bed to the nurse call system wall outlet, and forwards communications received from the nurse call system wall outlet to the bed.

SUMMARY

According to various embodiments, the present disclosure provides an improved system for helping to ensure that one or more conditions onboard a patient support apparatus, such as a bed, are synced with one or more corresponding conditions onboard the headwall unit, and vice versa, thereby helping to ensure that errors and/or other undesirable conditions do not take place in response to a mismatch between the bed conditions and the headwall conditions. The patient support apparatuses and headwall units disclosed herein are therefore configured to effectuate a syncing process that ensures that some of the bed conditions are synced with some of the headwall conditions, and some of the headwall conditions are synced with the bed conditions when the communication link is initially established.

According to a first embodiment of the present disclosure, a headwall unit is provided that is adapted to be mounted to a headwall of a room in a healthcare facility and used as part of the communication link between a patient support apparatus and a nurse call system. The headwall unit includes a nurse call interface, a first wireless transceiver, and a controller. The nurse call interface is adapted to electrically couple to a wall outlet mounted in the headwall, and it includes a set of pins adapted to electrically couple to a plurality of conductors defined in the wall outlet when the nurse call interface is coupled to the wall outlet. Each of the pins are adapted to be in different electrical states. The first wireless transceiver is adapted to wirelessly communicate with a second wireless transceiver positioned onboard the patient support apparatus when the patient support apparatus is positioned adjacent to the headwall unit. The controller is adapted to use the first wireless transceiver to establish a communication link with the patient support apparatus. In response to the communication link being established, the controller is configured to perform the following: (a) receive a plurality of state values from the patient support apparatus; and sync the electrical states of a subset of the set of pins to match the state values received from the patient support apparatus.

According to another aspect of the present disclosure, a first one of the state values received from the patient support apparatus defines an on or off state of a reading light. The reading light is adapted to provide illumination to a patient on the patient support apparatus.

In some embodiments, a second one of the state values received from the patient support apparatus defines an on or off state of a room light. The room light is adapted to provide illumination to an entire room in which the headwall unit it positioned.

In some embodiments, a first one of the state values received from the patient support apparatus defines an on or off state of a nurse call request. The nurse call request is adapted to notify a nurse call system coupled to the wall outlet of a patient's desire to speak with a nurse.

In some embodiments, a first one of the state values received from the patient support apparatus defines an on or off state of a priority alert signal. The priority alert signal is adapted to notify a nurse call system of a priority event occurring on the patient support apparatus.

In some embodiments, a first one of the state values received from the patient support apparatus defines an on or off state of a television control signal, and the television control signal is adapted to instruct a television to be turned on or off.

The headwall unit, in some embodiments, further comprises a third wireless transceiver adapted to wirelessly communicate with a fourth wireless transceiver positioned onboard the patient support apparatus when the patient support apparatus is positioned adjacent to the headwall unit.

In some embodiments, the communication link is established when both the first wireless transceiver and the third wireless transceiver are in communication with the second and fourth wireless transceivers, respectively, onboard the patient support apparatus.

In some embodiments, the first wireless transceiver is a radio frequency transceiver and the third wireless transceiver is an infrared transceiver.

The controller, in some embodiments, is further adapted to send a second plurality of state values to the patient support apparatus in response to the communication link being established. The second plurality of state values correspond to a current electrical state of a second subset of the set of pins that is different from the subset.

The controller, in some embodiments, is further adapted to receive audio signals from the patient support apparatus via the first wireless transceiver and to forward the audio signals to at least one of the pins.

The controller, in some embodiments, is further adapted to receive an exit alert message from the patient support apparatus and to change an electrical state of at least one of the pins in response to receiving the exit alert message.

In some embodiments, the headwall unit further includes a memory in which is stored a unique identifier that uniquely identifies the headwall unit, and the controller is further adapted to forward the unique identifier to the patient support apparatus using the first wireless transceiver.

The controller, in some embodiments, is further adapted to receive a configuration message via the first wireless transceiver. The configuration message includes an identification of a first pair of the pins that must be electrically shorted together to avoid triggering a cord-out alert in a nurse call system coupled to the wall outlet.

The controller, in some embodiments, is further adapted to receive a new configuration message via the first wireless transceiver which includes a new identification of a second pair of pins that must be electrically shorted together to avoid triggering the cord-out alert. The second pair of pins is different from the first pair of pins.

According to another embodiment of the present disclosure, a patient support apparatus is provided. The patient support apparatus includes a support surface, a first wireless transceiver, and a controller. The support surface is adapted to support a patient thereon. The first wireless transceiver is adapted to wirelessly communicate with a second wireless transceiver positioned onboard a headwall unit mounted to a headwall of room in a healthcare facility. The controller is adapted to use the first wireless transceiver to establish a communication link with the headwall unit and to perform the following in response to the communication link being established: (a) receive a plurality of headwall state values from the headwall unit; and (b) sync a plurality of patient support apparatus state values to match the headwall state values received from the headwall unit.

According to another aspect of the present disclosure, the patient support apparatus further comprises a nurse answer light adapted to be illuminated when a remotely positioned nurse answers a call from the patient, and a first one of the headwall state values defines an on or off state of the nurse answer light.

In some embodiments, a nurse call light is adapted to be illuminated when the patient calls a remotely positioned nurse, and a first one of the headwall state values defines an on or off state of the nurse call light.

In some embodiments, the patient support apparatus further comprises a cable detector adapted to detect a presence of a cable connecting the patient support apparatus to a wall outlet defined in the headwall, and a first one of the headwall state values defines an enabled or disabled state of the cable detector.

In some embodiments, the patient support apparatus further comprises a memory in which is stored a configuration setting of the headwall unit, and a first one of the headwall state values defines a configured state or an unconfigured state of the headwall unit.

In some embodiments, the patient support apparatus further comprises a memory in which is stored a television setting of a television coupled to the headwall unit, and a first one of the headwall state values defines a type of the television.

In some embodiments, the patient support apparatus further comprises a memory in which is stored a cable setting of a cable extending between the headwall unit and a wall outlet defined in the headwall, and a first one of the headwall state values defines a connected state or an unconnected state of the cable.

In some embodiments, the patient support apparatus further comprises a memory in which is stored an interlock setting of a pair of pins of the headwall unit, and a first one of the headwall state values defines an electrically shorted state or unshorted state of the pair of pins.

In some embodiments, the patient support apparatus further comprises a third wireless transceiver adapted to wirelessly communicate with a fourth wireless transceiver positioned onboard the headwall unit when the patient support apparatus is positioned adjacent to the headwall unit.

The communication link, in some embodiments, is established when both the first wireless transceiver and the third wireless transceiver are in communication with the second and fourth wireless transceivers, respectively, onboard the headwall unit.

In some embodiments, the first wireless transceiver is a radio frequency transceiver and the third wireless transceiver is an infrared transceiver.

The controller, in some embodiments, is further adapted to send audio signals to the headwall unit via the first wireless transceiver that are to be forwarded by the headwall unit to a wall outlet integrated into the headwall.

In some embodiments, the patient support apparatus further comprises an exit detection system adapted to detect a patient exit from the support surface. In such embodiments, the controller may be further adapted to send an exit alert message to the headwall unit via the first wireless transceiver that is to be forwarded by the headwall unit to a wall outlet integrated into the headwall.

The patient support apparatus, in some embodiments, further comprises a memory in which is stored a first unique identifier that uniquely identifies the patient support apparatus; and a network transceiver adapted to communicate with a computer network of the healthcare facility. In such embodiments, the controller may be further adapted to receive a second unique identifier of the headwall unit from the headwall unit and to forward both the first and second unique identifiers to a server on the computer network via the network transceiver.

In some embodiments, the patient support apparatus is a bed or a stretcher that includes a plurality of wheels, a plurality of siderails, and a height-adjustable litter frame. Still further, in some embodiments, the sync described herein takes places immediately after the communication link is established, such as within a second or two, although other time frames may be used.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 8 is a table of settings for the patient support apparatus and headwall unit that are synced shortly after the communication link is established between the patient support apparatus and headwall unit;

FIG. 11 is a chart of a prior art example of the functions of the pins of a 37-pin cable often used in existing healthcare facilities.

DETAILED DESCRIPTION OF THE EMBODIMENTS

Figure 1:
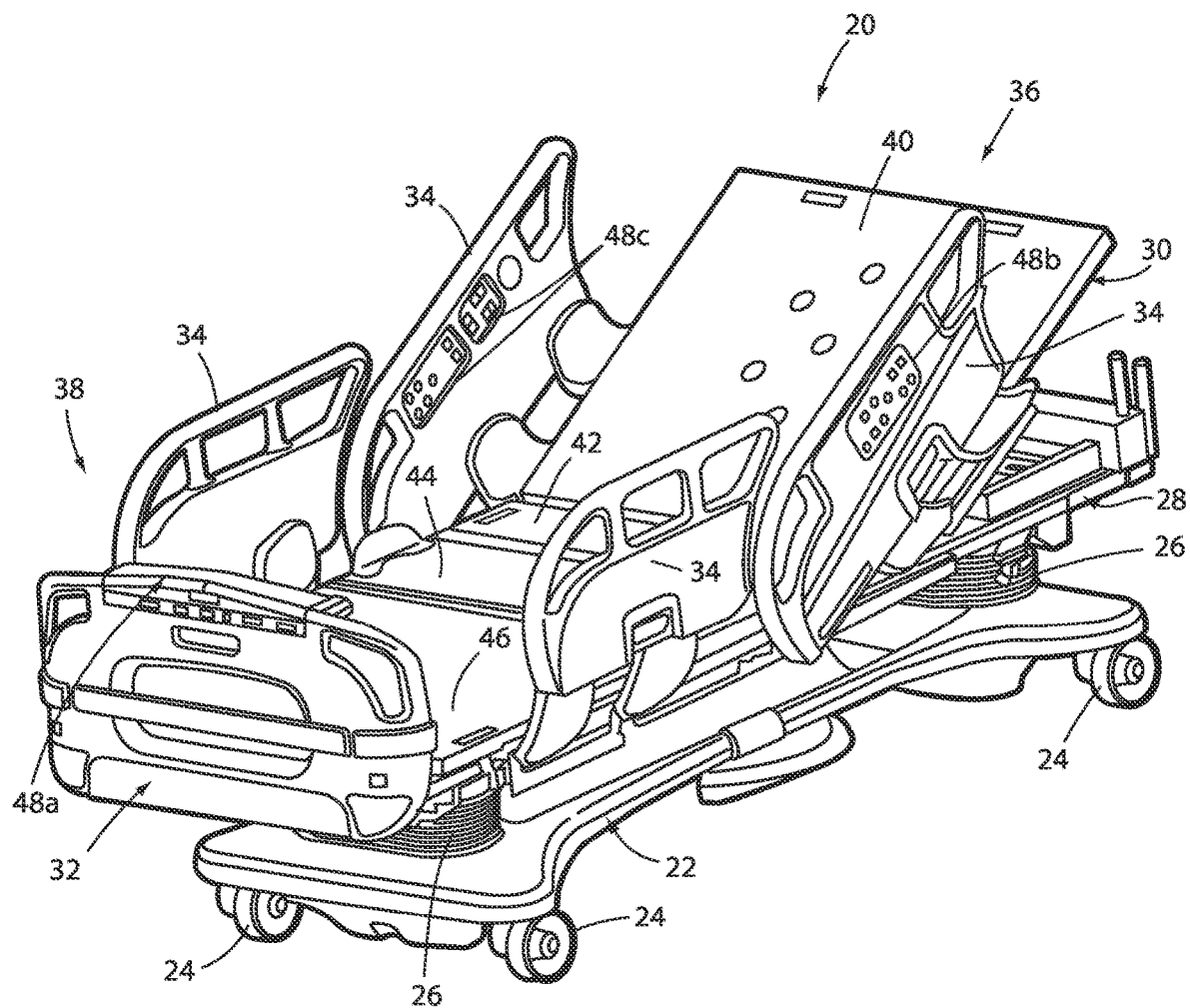
FIG. 1 is a perspective view of a patient support apparatus according to a first embodiment of the present disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, a chair, or any other patient support structure that communicates with a nurse call outlet of a conventional nurse call system.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a footboard 32 and a plurality of side rails 34. Side rails 34 are all shown in a raised position in FIG. 1 but are each individually movable to a lower position in which ingress into, and egress out of, patient support apparatus 20 is not obstructed by the lowered side rails 34.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. Patient support apparatus 20 is designed so that when an occupant lies thereon, his or her head will be positioned adjacent head end 36 and his or her feet will be positioned adjacent foot end 38.

Litter frame 28 provides a structure for supporting support deck 30, footboard 32, and side rails 34. Support deck 30 provides a support surface for a mattress (not shown in FIG. 1), such as, but not limited to, an air, fluid, or gel mattress. Alternatively, another type of soft cushion may be supported on support deck 30 so that a person may comfortably lie and/or sit thereon. The top surface of the mattress or other cushion forms a support surface for the occupant.

Support deck 30 is made of a plurality of sections, some of which are pivotable about generally horizontal pivot axes. In the embodiment shown in FIG. 1, support deck 30 includes a head section 40, a seat section 42, a thigh section 44, and a foot section 46. Head section 40, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 44 and foot section 46 may also be pivotable about generally horizontal pivot axes.

Patient support apparatus 20 further includes a plurality of control panels 48 that enable a user of patient support apparatus 20, such as a patient and/or an associated caregiver, to control one or more aspects of patient support apparatus 20. In the embodiment shown in FIG. 1, patient support apparatus 20 includes a footboard control panel 48a, a pair of outer side rail control panels 48b (only one of which is visible), and a pair of inner side rail control panels 48c (only one of which is visible). Footboard control panel 48a and outer side rail control panels 48b are intended to be used by caregivers, or other authorized personnel, while inner side rail control panels 48c are intended to be used by the patient associated with patient support apparatus 20. Each of the control panels 48 includes a plurality of controls 126 (FIG. 6), although each control panel 48 does not necessarily include the same controls and/or functionality. FIG. 7 illustrates one example of a patient control panel 48c, although it will be understood that other types patient control panels 48c may be used.

Among other functions, controls 126 (FIG. 6) of control panel 48a allow a user to control one or more of the following: change a height of litter frame 28, raise or lower head section 40, activate and deactivate a brake for wheels 24, arm and disarm an exit detection system, etc. One or both of the inner siderail control panels 48c also include at least one control that enables a patient to call a remotely located nurse (or other caregiver). In addition to the nurse call control, one or both of the inner siderail control panels 48c also include one or more controls for controlling one or more features of one or more room devices positioned within the same room as the patient support apparatus 20. As will be described in more detail below, such room devices include, but are not necessarily limited to, a television, a reading light, and/or a room light. With respect to the television, the features that may be controllable by one or more controls on control panel 48c include, but are not limited to, the volume, the channel, the closed-captioning, and/or the power state of the television. With respect to the room and/or night lights, the features that may be controlled by one or more controls on control panel 48c include the on/off state and/or the brightness level of these lights.

Footboard control panel 48a is implemented in the embodiment shown in FIG. 1 as a control panel having a lid (flipped down in FIG. 1) underneath which is positioned a plurality of controls. As with all of the controls of the various control panels 48, the controls of control panel 48a may be implemented as buttons, dials, switches, or other devices. Any of control panels 48a-c may also include a display for displaying information regarding patient support apparatus 20. The display is a touchscreen in some embodiments.

In some embodiments, footboard control panel 48a may take on the form of the footboard control panel 54a disclosed in commonly assigned PCT patent application serial number PCT/US2021/32426 filed May 14, 2021, by applicant Stryker Corporation and entitled PATIENT SUPPORT APPARATUSES WITH HEADWALL COMMUNICA- TION, the complete disclosure of which is incorporated herein by reference. Additionally, or alternatively, patient control panel 48c may take on the form of the patient control panel 54c disclosed in the aforementioned PCT patent application. Other types of footboard control panels 48a-c may, of course, be implemented.

Figure 2:
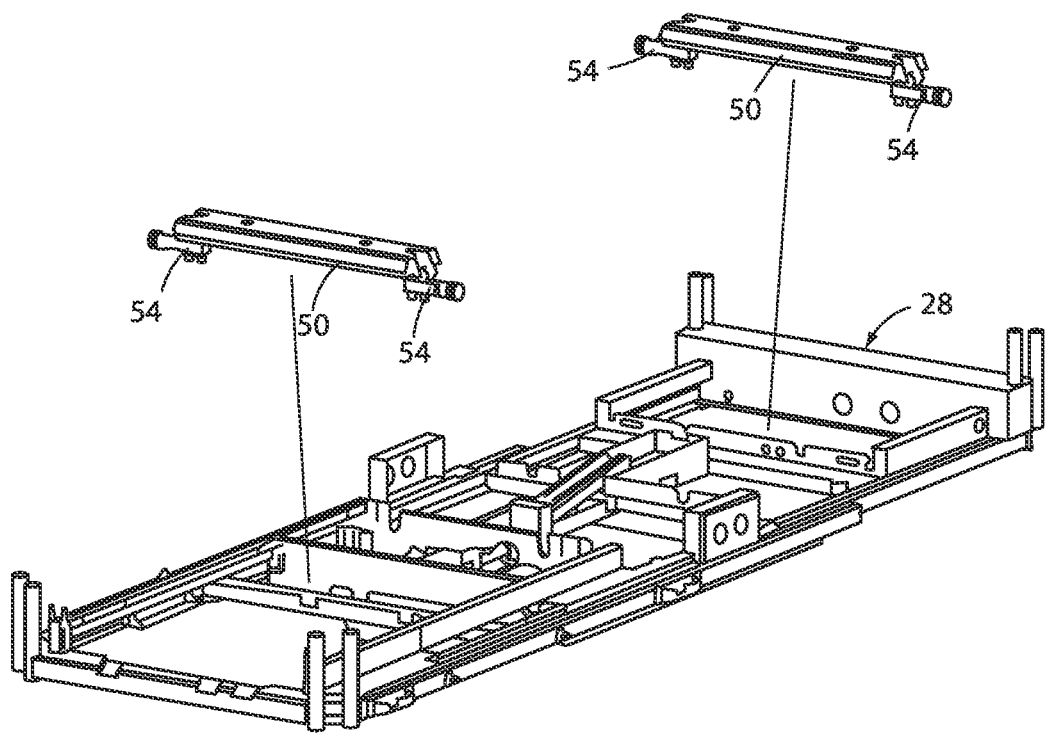
FIG. 2 is a perspective view of a litter frame and a pair of lift header assemblies of the patient support apparatus.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 52 (FIG. 3) of a first one of the lifts 26, and a second one of the lift header assemblies 50 is coupled to the top 52 of the second one of the lifts 26. Each lift header assembly 50 includes a pair of force sensors 54, which will be described herein as being load cells, but it will be understood that force sensors 54 may be other types of force sensors besides load cells. The illustrated embodiment of patient support apparatus 20 includes a total of four load cells 54, although it will be understood by those skilled in the art that different numbers of load cells may be used in accordance with the principles of the present disclosure. Load cells 54 are configured to support litter frame 28. More specifically, load cells 54 are configured such that they provide complete and exclusive mechanical support for litter frame 28 and all of the components that are supported on litter frame 28 (e.g. support deck 30, footboard 32, side rails 34, etc.). Because of this construction, load cells 54 are adapted to detect the weight of not only those components of patient support apparatus 20 that are supported by litter frame 28 (including litter frame 28 itself), but also any objects or persons who are wholly or partially being supported by support deck 30.

Figure 3:
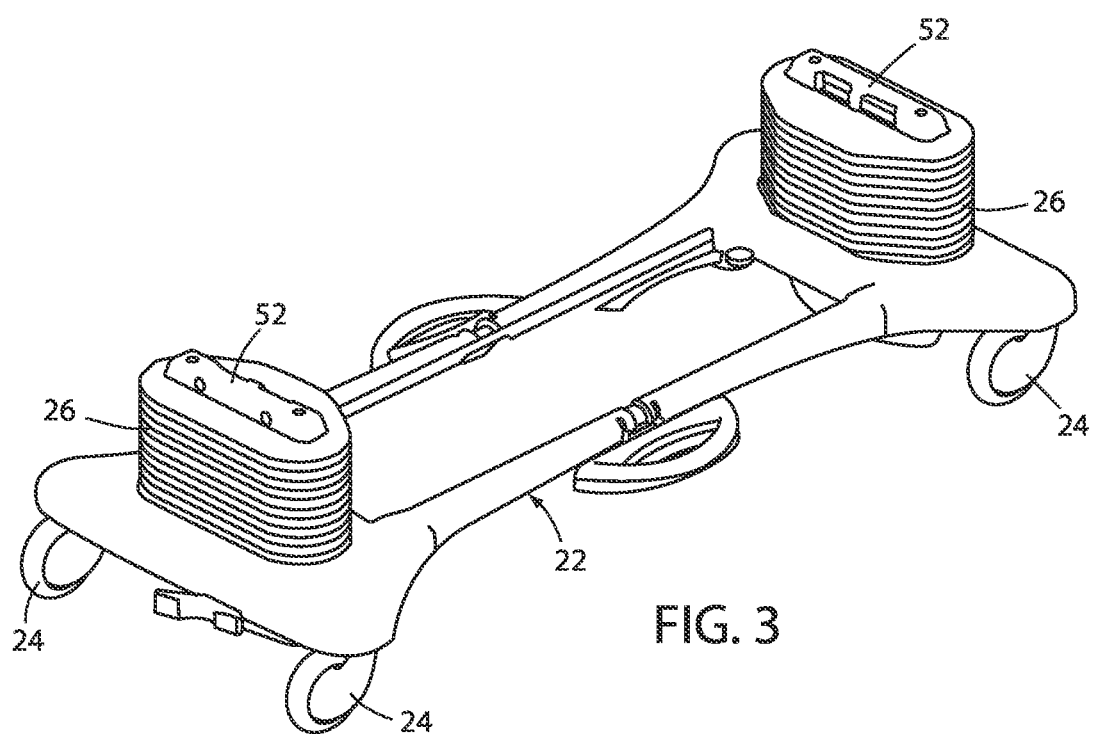
FIG. 3 is a perspective view of a base and a pair of lifts of the patient support apparatus.

The mechanical construction of patient support apparatus 20, as shown in FIGS. 1-3, is the same as, or nearly the same as, the mechanical construction of the Model 3002 S3 bed manufactured and sold by Stryker Corporation of Kalamazoo, Michigan. This mechanical construction is described in greater detail in the Stryker Maintenance Manual for the MedSurg Bed, Model 3002 S3, published in 2010 by Stryker Corporation of Kalamazoo, Michigan, the complete disclosure of which is incorporated herein by reference. It will be understood by those skilled in the art that patient support apparatus 20 can be designed with other types of mechanical constructions, such as, but not limited to, those described in commonly assigned, U.S. Pat. No. 7,690,059 issued to Lemire et al., and entitled HOSPITAL BED; commonly assigned U.S. Pat. Publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION; and/or commonly assigned, U.S. Pat. No. 10,130,536 to Roussy et al., entitled PATIENT SUPPORT USABLE WITH BARIATRIC PATIENTS, the complete disclosures of all of which are also hereby incorporated herein by reference. The mechanical construction of patient support apparatus 20 may also take on forms different from what is disclosed in the aforementioned references.

Load cells 54 are part of an exit detection system 56 (FIG. 6) that, when armed, issues an alert when the patient exits from patient support apparatus 20. Exit detection system 56 is adapted to be armed via control panel 48a. After being armed, exit detection system 56 determines when an occupant of patient support apparatus 20 has left, or is likely to leave, patient support apparatus 20, and issues an alert and/or notification to appropriate personnel so that proper steps can be taken in response to the occupant's departure (or imminent departure) in a timely fashion. In at least one embodiment, exit detection system 56 monitors the center of gravity of the patient using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. In other embodiments, exit detection system 56 determines if the occupant is about to exit, or already has exited, from patient support apparatus 20 by determining a distribution of the weights detected by each load cell 54 and comparing the detected weight distribution to one or more thresholds. In such embodiments, the center of gravity may or may not be explicitly calculated.

Other manners for functioning as an exit detection system are also possible. These include, but are not limited to, any of the manners disclosed in the following commonly assigned patent applications: U.S. patent application Ser. No. 14/873,734 filed Oct. 2, 2015, by inventors Marko Kostic et al. and entitled PERSON SUPPORT APPARATUS WITH MOTION MONITORING; U.S. patent publication 2016/0022218 filed Mar. 13, 2014, by inventors Michael Hayes et al. and entitled PATIENT SUPPORT APPARATUS WITH PATIENT INFORMATION SENSORS; and U.S. patent application Ser. No. 15/266,575 filed Sep. 15, 2016, by inventors Anuj Sidhu et al. and entitled PERSON SUPPORT APPARATUSES WITH EXIT DETECTION SYSTEMS, the complete disclosures of all of which are incorporated herein by reference. Further, in some embodiments, load cells 54 may be part of both an exit detection system and a scale system that measures the weight of a patient supported on support deck 30. The outputs from the load cells 54 are processed, in some embodiments, in any of the manners disclosed in commonly assigned U.S. patent application Ser. No. 62/428,834 filed Dec. 1, 2016, by inventors Marko Kostic et al. and entitled PERSON SUPPORT APPARATUSES WITH LOAD CELLS, the complete disclosure of which is incorporated herein by reference.

Figure 4:
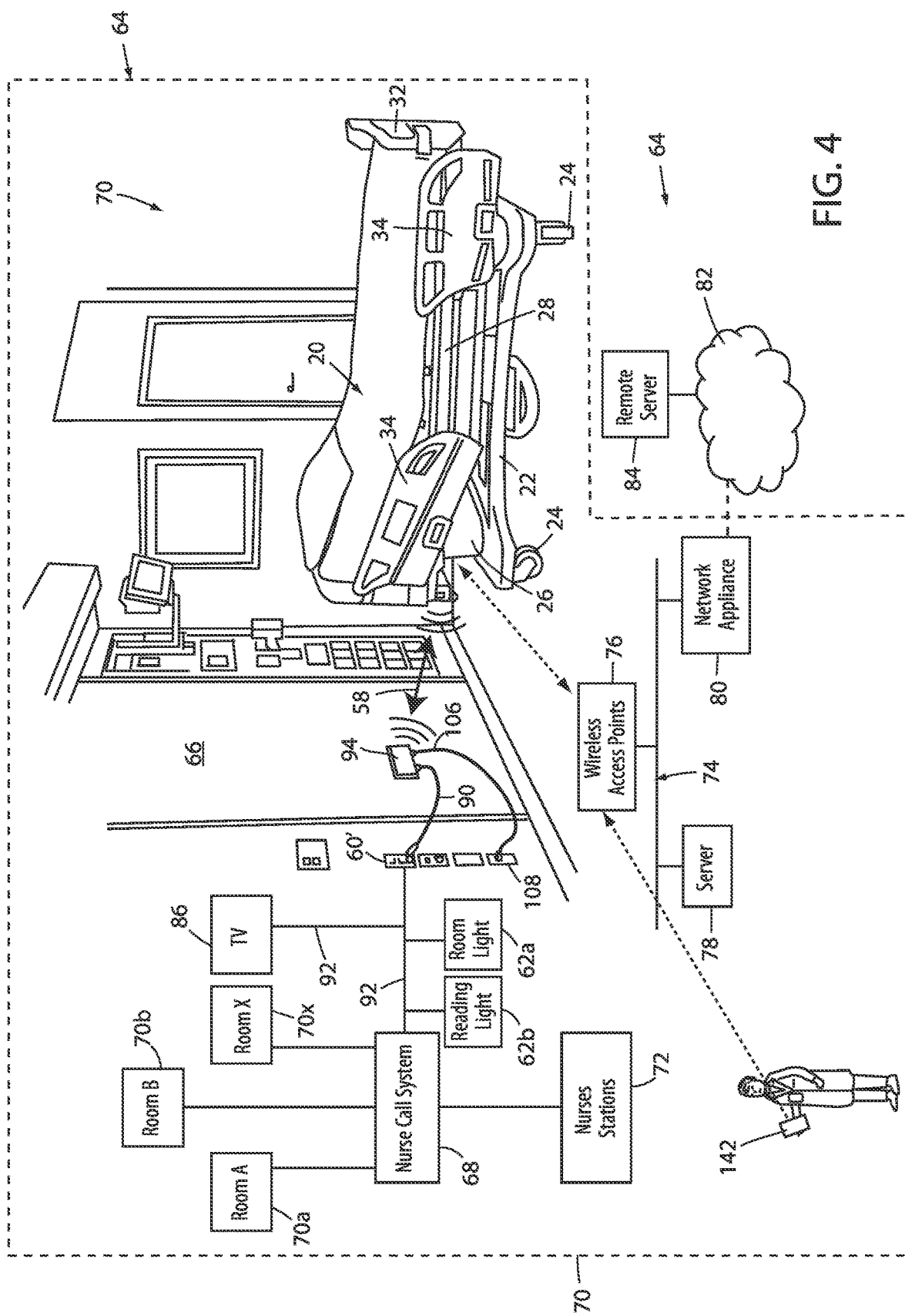
FIG. 4 is a diagram of the patient support apparatus, a wireless headwall unit, and a wireless communication link between the patient support apparatus and a wall outlet of a nurse call system.

Regardless of how implemented, patient support apparatus 20 is adapted to communicate an alert when the exit detection system is armed and detects that a patient is about to, or has, exited. One manner in which the alert is communicated to a conventional nurse call system 68 is shown in FIG. 4. Patient support apparatus 20 communicates with a nurse call system 68, and vice versa, through a communication link 58 that is established between patient support apparatus 20 and a conventional nurse call wall outlet 60. Communication link 58 is a wireless communication link. In addition to forwarding an exit detection alert over communication link 58 from patient support apparatus 20 to nurse call system 68, communication link 58 may be used for communicating a variety of other information.

One example of such information are the audio signals of the patient and a remotely positioned nurse. That is, a patient onboard patient support apparatus 20 is able to communicate with a remotely positioned nurse by speaking into a microphone onboard patient support apparatus 20, and patient support apparatus 20 forwards these audio signals to a remotely positioned nurse by transmitting them over communication link 58 to wall outlet 60, which is in communication with nurse call system 68, as will be discussed in greater detail below. Similarly, a remotely positioned nurse is able to speak into a microphone coupled to the nurse call system and have his/her voice signals forwarded to wall outlet 60, which are then transmitted over communication link 58 to a speaker onboard patient support apparatus 20.

FIG. 4 illustrates additional details of a typical healthcare facility 64. As shown therein, healthcare facility 64 includes a headwall 66, nurse call system 68, a plurality of rooms 70 (70a, 70b ... 70x), one or more nurses' stations 72, a local area network 74, one or more wireless access points 76, a patient support apparatus server 78, and one or more network appliances 80 that couple LAN 74 to the internet 82, thereby enabling server 78 and other applications on LAN 74 to communicate with computers outside of healthcare facility 64, such as, but not limited to, a geographically remote server 84. Wall outlet 60 is typically electrically coupled by one or more conductors 92 to a television 86 and one or more room devices (e.g. a room light 62a, a reading light 62b, etc.). It will be understood by those skilled in the art, however, that the healthcare facility infrastructure shown in FIG. 4 may vary widely from healthcare facility to healthcare facility.

For example, patient support apparatus 20 may be used in healthcare facilities having no wireless access points 76, no connection to the internet 82 (e.g. no network appliances 80), and/or no patient support apparatus server 78. Still further, local area network 74 may include other and/or additional servers installed thereon, and/or room 70, in some healthcare facilities 64, may be semi-private room having multiple patient support apparatuses 20 and multiple wall outlets 60. Still other variations are possible. It will therefore be understood that the particular healthcare facility infrastructure shown in FIG. 4 is merely illustrative, and that patient support apparatus 20 is constructed to be communicatively coupled to healthcare facility communication infrastructures which are arranged differently from that of FIG. 4, some of which are discussed in greater detail below.

As is shown in FIG. 4, patient support apparatus 20 is adapted to be communicatively coupled to the wall outlet 60 on headwall 66 by way of a wireless communication link 58 that wirelessly couples patient support apparatus 20 to a wireless headwall unit 94. Headwall unit 94, in turn, is coupled by way of a cable 90 to wall outlet 60. Headwall unit 94 and patient support apparatus 20 are able to communicate wirelessly with each other in a bidirectional fashion. That is, messages can be wirelessly sent from patient support apparatus 20 to headwall unit 94, and messages can be wirelessly sent from headwall unit 94 to patient support apparatus 20.

Although not shown in FIG. 4, patient support apparatus 20 may further be configured to be able to communicate with wall outlet 60 via a cable, if desired. When such wired communication is desired, a nurse call cable 90 is connected directly from patient support apparatus 20 to wall outlet 60. Unless wall outlet 60 has room for two cable plugs, the end of cable 90 shown in FIG. 4 that is plugged into wall outlet 60 is removed in order to allow the cable from patient support apparatus 20 to be inserted therein. Alternatively, the end of the cable 90 shown in FIG. 4 that is plugged into headwall unit 94 may be removed and plugged into patient support apparatus 20. However attained, once a cable 90 is coupled between patient support apparatus 20 and wall outlet 60, a wired connection is established that bypasses headwall unit 94 (if present).

Wall outlet 60 is coupled to one or conductors 92 that electrically couple the wall outlet 60 to nurse call system 68 and to one or more other devices, such as television 86, room light 62a, and/or reading light 62b. Conductors 92 are typically located behind headwall 66 and not visible. In some healthcare facilities, conductors 92 may first couple to a room interface board that includes one or more electrical connections electrically coupling the room interface board to television 86 and/or nurse call system 68. Still other communicative arrangements for coupling wall outlet 60 to nurse call system 68 and television 86 are possible.

Communication link 58 (FIG. 4) enables patient support apparatus 20 to communicate with nurse call system 68, television 86, room light 62a, and/or reading light 62b. A patient supported on patient support apparatus 20 who activates a nurse call control on patient support apparatus 20 causes a signal to be conveyed via communication link 58 to the nurse call system 68, which then sends a notification to one or more remotely located nurses (e.g. nurses at one of the nurses' stations 72). If the patient uses a TV control positioned on one of the control panels (e.g. control 126k of control panel 48c; see FIG. 7) to change a channel or change the volume of television 86, the control conveys a signal along link 58 to the wall outlet 60, and the signal is thereafter passed from outlet 60 to television 86. Similarly, if the patient uses a room light or reading light control on one of the control panels, he or she is able to turn on or off the room light 62a and reading light 62b.

As will be discussed in greater detail below, outlet 60 often includes a plurality of pins (e.g. 37 pins), and the audio signals that are passed between the patient and a remotely positioned nurse are transmitted over a separate set of pins than the pins that transmits control signals for controlling television 86. Additional pins are used for communicating other information between patient support apparatus 20 and nurse call system 68 and/or other devices positioned within room 70 (e.g. television 86, room light 62a, reading light 62b).

Figure 5:
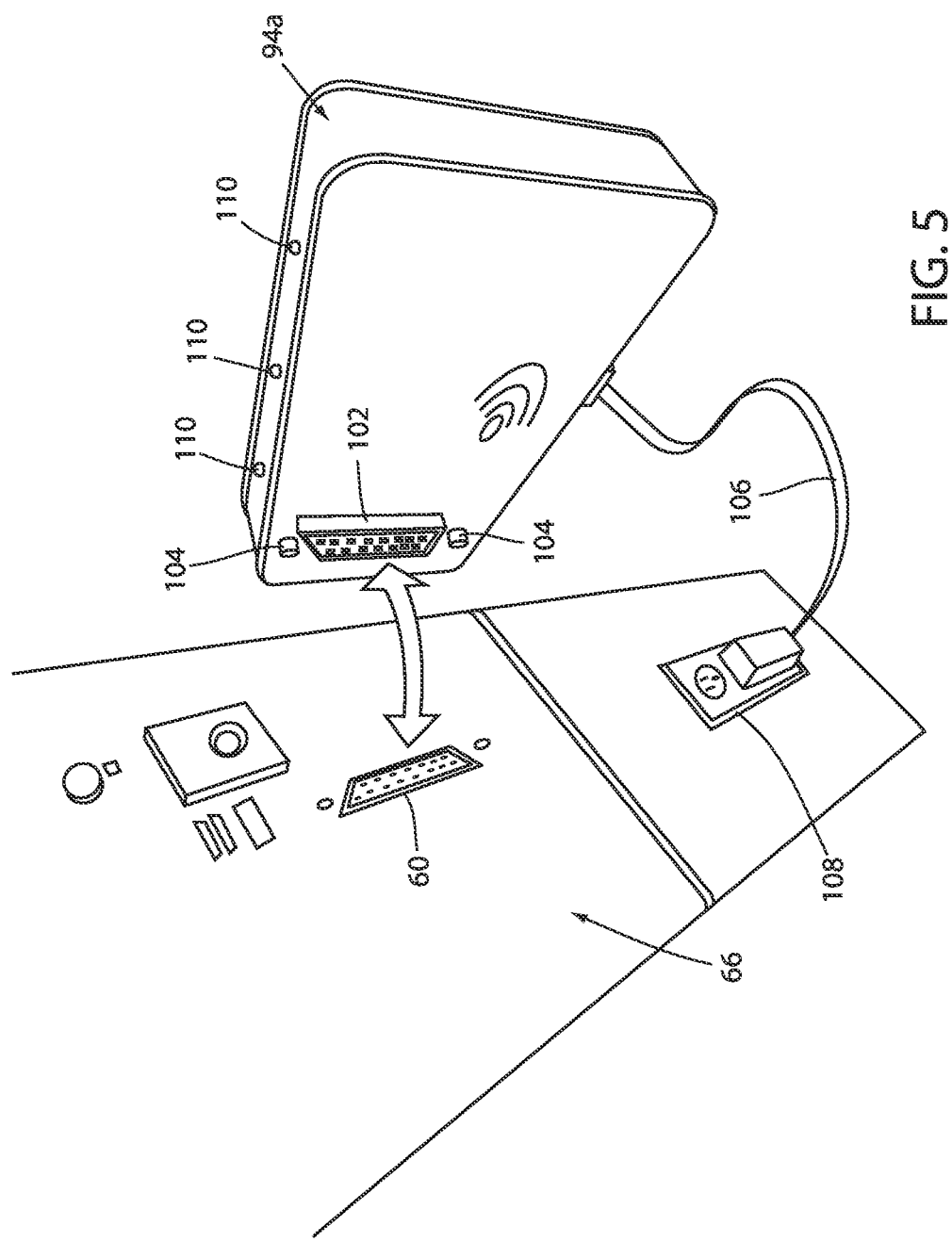
FIG. 5 is a diagram of an alternative wireless headwall unit.

FIG. 5 illustrates an alternative embodiment of a headwall unit 94a according to another embodiment of the present disclosure. Headwall unit 94a differs from headwall unit 94 in that, rather than including a connector for a cable 90, it is adapted to plug directly into wall outlet 60 via a connector 102. Connector 102 is thus shaped and dimensioned to be frictionally maintained in an electrically coupled state to outlet 60, and to support the entire headwall unit 94a. One or more alignment posts 104 may be included with connector 102 in order to more securely retain headwall unit 94a to wall outlet 60, if desired. Connector 102 may be the same as, or nearly the same as, an end of a cable 90, thereby allowing either a cable from headwall unit 94, or connector 102 from headwall unit 94a, to be inserted into wall outlet 60.

In the embodiment shown in FIG. 5, connector 102 is a 37 pin connector that includes 37 pins adapted to be inserted into 37 mating sockets of wall outlet 60. Such 37 pin connections are one of the most common types of connectors found on existing headwalls of medical facilities for making connections to the nurse call system 68. Such 37 pin connectors, however, are not the only type of connectors, and it will be understood that headwall unit 94a can utilize different types of connectors 102 (whether integrated therein or attached to a cable) that are adapted to electrically couple to different types of nurse call outlets 60. One example of such an alternative wall outlet 60 and cable is disclosed in commonly assigned U.S. patent application Ser. No. 14/819,844 filed Aug. 6, 2015, by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of wall outlets 60 and corresponding cable connectors 102 may be utilized.

Other than the absence of a connector for a cable 90, headwall unit 94a may be the same as headwall unit 94, and the following description of headwall unit 94 will apply equally to both headwall unit 94 and headwall unit 94a.

Headwall unit 94 of FIG. 4 (and headwall unit 94*a* of FIG. 5) include a power cable 106 having an end adapted to be inserted into a conventional electrical outlet 108. Power cable 106 enables headwall unit 94 to receive power from the mains electrical supply via outlet 108. It will be appreciated that, in some embodiments, headwall unit 94 is battery operated and cable 106 may be omitted. In still other embodiments, headwall unit 94 may be both battery operated and include cable 106 so that in the event of a power failure, battery power supplies power to headwall unit 94, and/or in the event of a battery failure, electrical power is received through outlet 108.

Headwall unit 94 may also include a plurality of status lights 110, such as are shown in FIG. 5. Status lights 110 provide visual indications about one or more aspects of headwall unit 94. For example, in some embodiments, the illumination of one of status lights 110 indicates that headwall unit 94 is in successful communication with nurse call system 68 and/or patient support apparatus 20. The illumination of one or more additional status lights 110 may also or alternatively indicate that power is being supplied to headwall unit 94 and/or the status of a battery included within headwall unit 94. Still further, in some embodiments, one or more of status lights 110 may be illuminated depending upon whether a nurse is talking to the patient, or vice versa.

Headwall unit 94 of FIG. 4 (and headwall unit 94*a* of FIG. 5) are adapted to wirelessly receive signals from patient support apparatus 20 and deliver the signals to wall outlet 60 in a manner that matches the way the signals would otherwise be delivered to wall outlet 60 if a conventional nurse call cable (e.g. cable 90) were connected between patient support apparatus 20 and wall outlet 60. In other words, patient support apparatus 20 and headwall unit 94 cooperate to provide signals to wall outlet 60 in a manner that is transparent to wall outlet 60 and nurse call system 68 such that these components cannot detect whether they are in communication with patient support apparatus 20 via wired or wireless communication. In this manner, a healthcare facility can utilize the wireless communication abilities of one or more patient support apparatuses 20 without having to make any changes to their existing wall outlet 60 or to their nurse call system 68.

In addition to sending signals received from patient support apparatus 20 to wall outlet 60, headwall unit 94 is also adapted to forward signals received from wall outlet 60 to patient support apparatus 20. Such bidirectional communication includes, but is not limited to, communicating audio signals between a person supported on patient support apparatus 20 and a nurse positioned remotely from patient support apparatus 20 (e.g. nurses' station 72). The audio signals received by headwall unit 94 from patient support apparatus 20 are forwarded to wall outlet 60, and the audio signals received by wall outlet 60 from nurse call system 68 are forwarded to one or more speakers onboard patient support apparatus 20.

Headwall unit 94 also communicates the data and signals it receives from patient support apparatus 20 to the appropriate pins of wall outlet 60. Likewise, it communicates the data and signals it receives and/or detects on the pins of wall outlet 60 to patient support apparatus 20 via wireless messages. The wireless messages include sufficient information for patient support apparatus 20 to discern what pins the messages originated from, or sufficient information for patient support apparatus 20 to decipher the information included in the message. In at least one embodiment, headwall unit 94 includes any and/or all of the same functionality as, and/or components of, the headwall units 76 disclosed in commonly assigned U.S. patent application Ser. No. 16/215,911 filed Dec. 11, 2018, by inventors Alexander Bodurka et al. and entitled HOSPITAL HEADWALL COMMUNICATION SYSTEM, the complete disclosure of which is incorporated herein by reference. Alternatively, or additionally, headwall unit 94 may include any and/or all of the same functionality as, and/or components of, the headwall interface 38 disclosed in commonly assigned U.S. patent publication 2016/0038361 published Feb. 11, 2016, entitled PATIENT SUPPORT APPARATUSES WITH WIRELESS HEADWALL COMMUNICATION, and filed by inventors Krishna Bhimavarapu et al., the complete disclosure of which is also incorporated herein by reference. Still further, headwall unit 94 and/or patient support apparatus 20 may include any of the functionality and/or components of the headwall units 140, 140*a* and/or patient support apparatuses 20, 20*a*, and/or 20*b* disclosed in commonly assigned U.S. patent application Ser. No. 62/833,943 filed Apr. 15, 2019, by inventors Alexander Bodurka et al. and entitled PATIENT SUPPORT APPARATUSES WITH NURSE CALL AUDIO MANAGEMENT, the complete disclosure of which is incorporated herein by reference.

Figure 6:
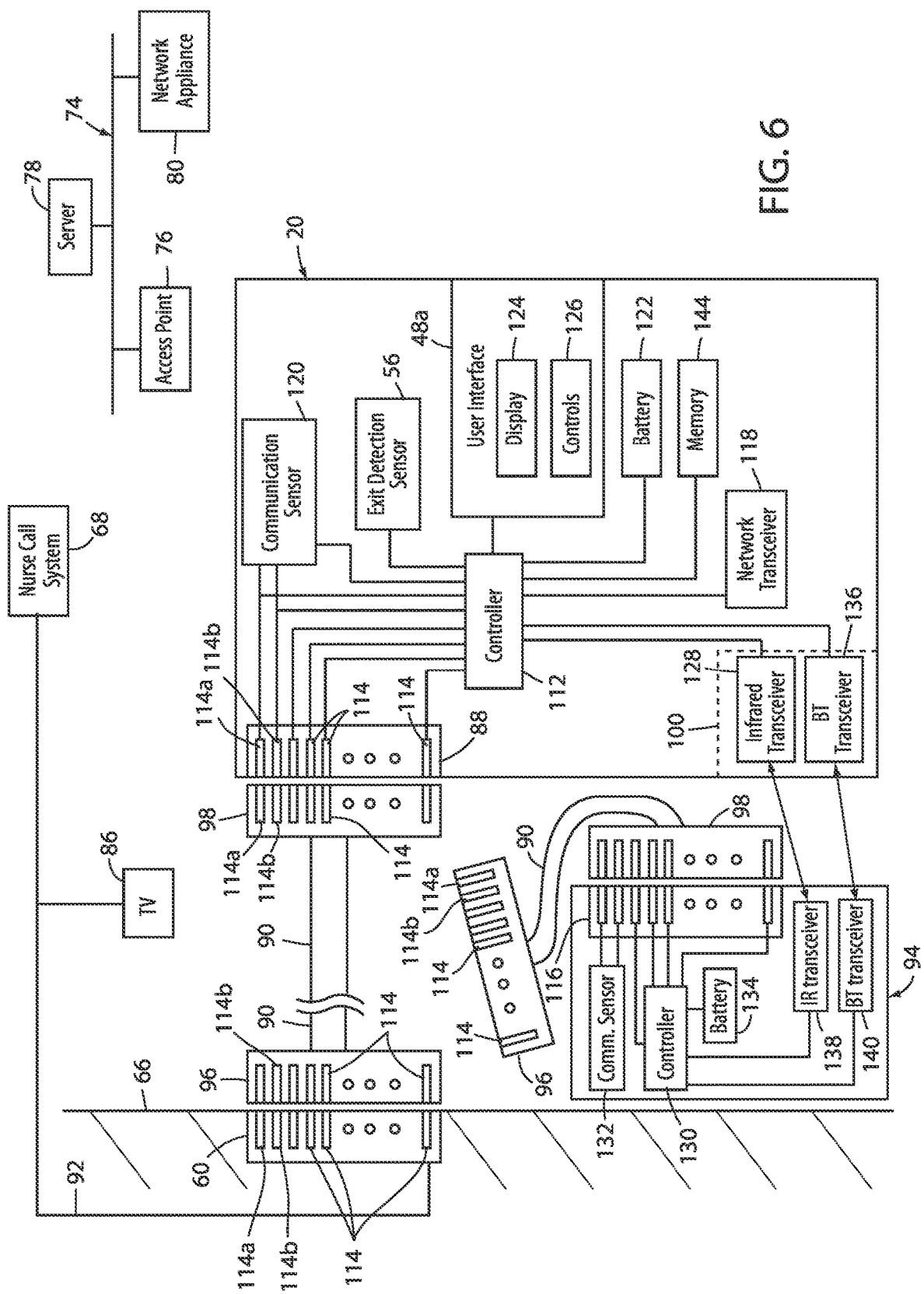
FIG. 6 is a block diagram of several of the structures of FIG. 4 showing some of the internal components of the headwall unit and the patient support apparatus.
Figure 7:
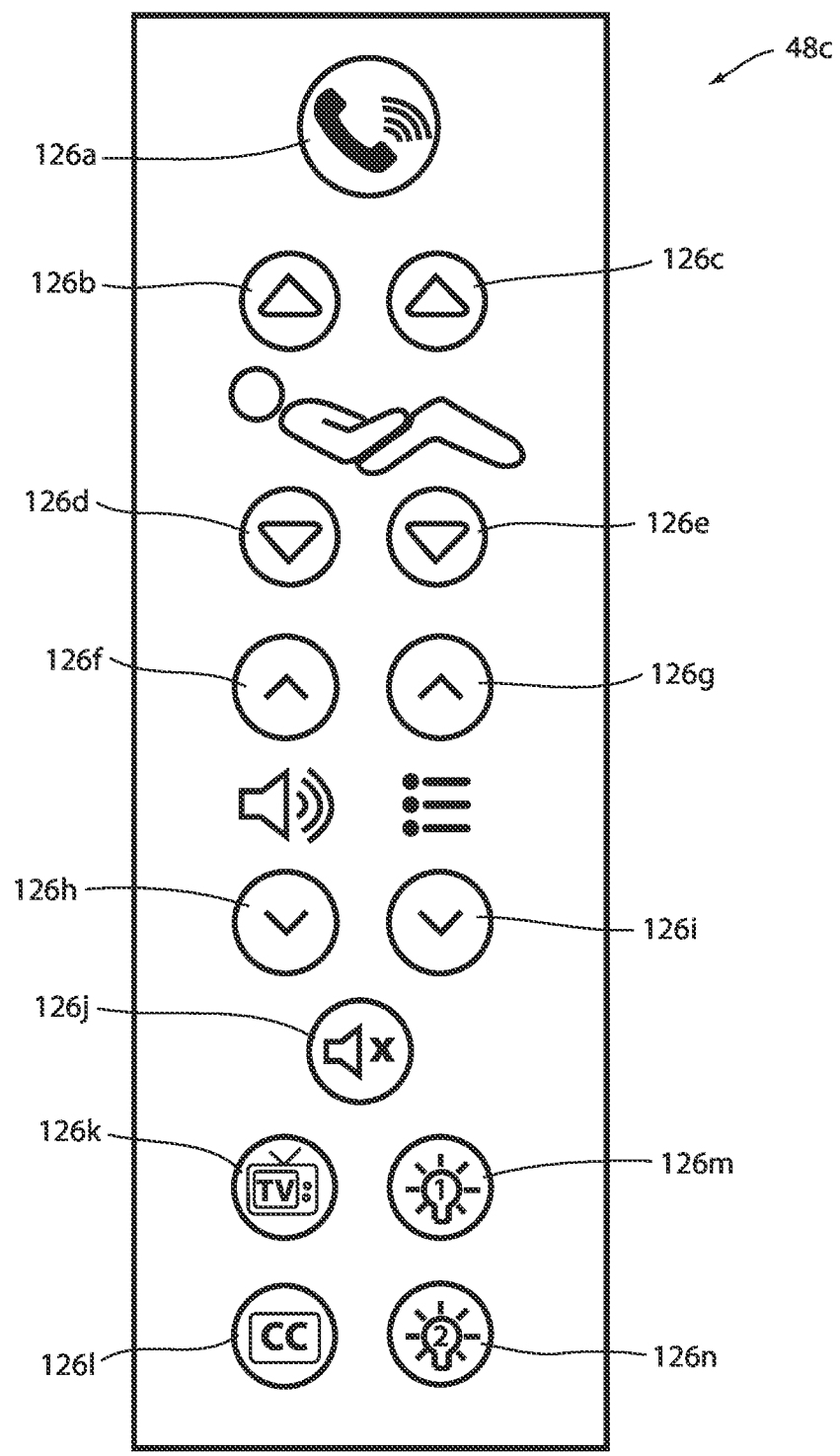
FIG. 7 is a plan view of an illustrative patient control panel of the patient support apparatus.
Figure 9:
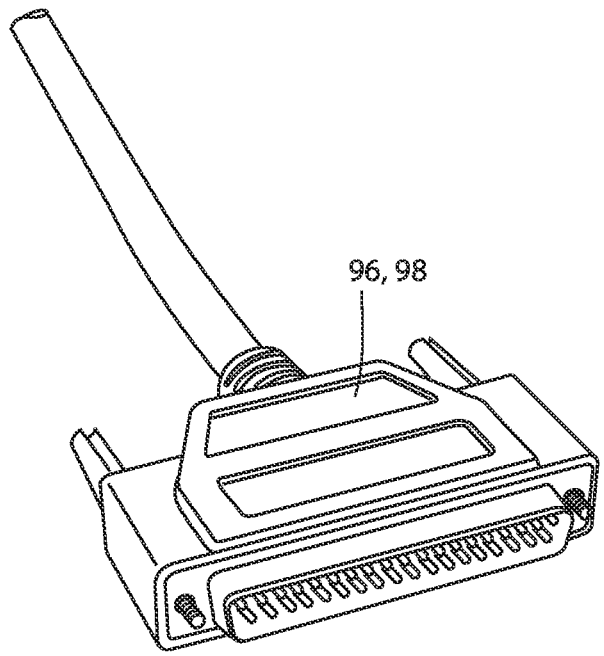
FIG. 9 is a perspective view of a prior art 37-pin male cable connector.

Cable 90 includes a first end having a first connector 96 and a second end having a second connector 98 (FIG. 6). First connector 96 is adapted to be plugged into wall outlet 60. Second connector 98 is adapted to be plugged into a cable interface 88 positioned on patient support apparatus 20. In many healthcare facilities 64, wall outlet 60 is configured as a 37-pin receptacle. In such facilities, cable 90 includes first and second connectors 96 and 98 having 37 pins (one of which may be a male connector and the other of which may be a female connector, although other combinations may be used). One example of a male 37-pin connector 96, 98 that may be used as first or second connector 96 or 98 is shown in FIG. 8. One example of a female 37-pin connector 96, 98 that may be used as first or second connector 96 or 98 is shown in FIG. 9. Other types of 37-pin connectors may also be used, depending upon the configuration of wall outlet 60. Still further, in some healthcare environments, wall outlet 60 includes fewer pins and/or has an arrangement of pins that is shaped to match a cable 90 having connectors different from what is shown in FIGS. 8 and 9. Patient support apparatus 20 and headwall unit 94 are adapted to communicate with all of these different types of wall outlets 60 via an appropriately selected cable (e.g. one with the proper connectors 96, 98 on its ends).

FIG. 6 illustrates further details regarding the manner in which patient support apparatus 20 communicates with wall outlet 60, and vice versa, as well as the structures involved with that communication. In the example of FIG. 6, patient support apparatus 20 has dual communication capabilities. That is, it is able to communicate with wall outlet 60 via either wireless communication link 58 or cable 90.

Patient support apparatus 20 includes cable interface 88 (FIG. 6), a wireless interface 100, a controller 112, a network transceiver 118, a communication sensor 120, exit detection system 56, a battery 122, a memory 144, and one or more control panels 48 (only control panel 48*a* is shown in FIG. 6, but it will be understood that the functions discussed below with respect to control panel 48*a* may be implemented on other ones of the control panels 48*b* and/or 48*c*).

Cable interface 88 is adapted to electrically couple to the plurality of pins 114 of cable connector 98. It will be understood that, although FIG. 6 shows a plurality of pins 114 for each of connectors 96 and 98 of cables 90, wall outlet 60, cable interface 88 of patient support apparatus 20, and a cable interface 116 of headwall unit 94, one or more of these devices (cable connectors 96, 98, cable interfaces 88, 116, and wall outlet 60) will include pin receptacles instead of pins. Such pin receptacles are adapted to receive and electrically couple to pins 114. Further, it will be understood that it does not matter which of these devices include pins and which includes pin receptacles so long as each connection between the devices include a combination of pins and pin receptacles that allow communication between the mated devices. Consequently, the term "pins" as used herein will refer to pins and/or pin receptacles.

In some embodiments, controller 112 is implemented as, and/or includes, one or more conventional microcontrollers. In other embodiments, controller 112 may be modified to use a variety of other types of circuits-either alone or in combination with one or more microcontrollers-such as, but not limited to, any one or more microprocessors, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by the microcontroller (if included) when carrying out the functions described herein, as well as the data necessary for carrying out these functions, are stored in a memory (e.g. memory 144) that is accessible to controller 112.

It will be understood that wall outlet 60, cables 90, and cable interfaces 88 and 116 are all illustrated in FIG. 6 as having only six pins. This is done merely for purposes of compact illustration. All of these components typically include 37 pins, although there are other wall outlets having different pin numbers and the principles of the present disclosure can be applied in healthcare facilities having these types of wall outlets as well. The pins that are not shown in FIG. 6 are used by other components of patient support apparatus 20 for other purposes. For example, one or more pins may be used to convey information to a room light 62*a* or reading lights 62*b* that is electrically coupled to conductor 92, such as a message or command indicating that the patient has pressed a control on patient support apparatus 20 to turn on or turn off a light (62*a* or 62*b*) in the particular room in which patient support apparatus 20 is located. Another pin may communicate the status of a component onboard patient support apparatus 20, such as, but not limited to whether one or more side rails 34 are in a down position (or an up position); whether the position of any of the side rails 34 changes from an initial state; whether a brake on patient support apparatus 20 is set; whether the exit detection system is armed; whether support deck 30 is at its lowest height; whether head section 40 has pivoted to less than a threshold angle (e.g. 30 degrees); and whether patient support apparatus 20 has been set to monitor a particular set of conditions. These various items of data are detected by one or more corresponding sensors onboard patient support apparatus 20 that are in communication with controller 112. Still others of the additional pins may be used for still other purposes.

Although FIG. 6 illustrates a number of the pins 114 of cable interface 88 being fed directly to controller 112, it will be understood that this is done merely for purposes of illustrative convenience, and that one or more of these pins 114 may be fed to one or more intermediary structures before being fed to controller 112. Such intermediary structures may include, but are not limited to, one or more relays and/or switches whose states are controlled by controller 112. Additionally, some pins may not be coupled to controller 112, but may be routed to other structures within patient support apparatus 20.

It will also be understood that, although FIG. 6 illustrates two cables 90-one extending from patient support apparatus 20 to outlet 60 and another one extending from headwall unit 94 to a free end, in actual usage within a particular room within a healthcare facility, only a single cable 90 will be used at any given time. Thus, patient support apparatus 20 will either be coupled to outlet 60 by a cable 90, or headwall unit 94 will be coupled to outlet 60 by a cable 90. In the former case, patient support apparatus 20 communicates with wall outlet 60 via wired communication, and in the latter case, patient support apparatus 20 communicates with wall outlet 60 via wireless communication link.

Battery 122 supplies electrical power to patient support apparatus 20 when its power cord (not shown) is not plugged into an external source of electrical energy (e.g. electrical outlet 108 of FIG. 4). Controller 112, either alone or in combination with other circuitry, may be adapted to monitor a charge state of battery 122 and/or to monitor one or more other characteristics of battery 122. When so adapted, controller 112 is adapted to issue an alert if battery 122 drops below a particular charge threshold while patient support apparatus 20 is not coupled to an external source of electrical power.

Controller 112 (FIG. 6) communicates with communication sensor 120, exit detection system 56, control panel 48*a*, network transceiver 118, memory 144, battery 122, cable interface 88, and wireless interface 100. Controller 112 uses wireless interface 100 to communicate wirelessly with headwall unit 94, and it uses cable interface 88 to communicate with wall outlet 60 via a cable 90.

In some embodiments, control panel 48*a* includes a display 124 (FIG. 6) and a plurality of controls 126. In some embodiments, the display 124 may take on the form and/or functionality of the display 64*a* disclosed in commonly assigned U.S. patent application Ser. No. 62/864,638 filed Jun. 21, 2019, by inventors Kurosh Nahavandi et al. and entitled PATIENT SUPPORT APPARATUS WITH CAREGIVER REMINDERS, the complete disclosure of which is incorporated herein by reference. Still other types of displays may also be used. Control panel 48*a* may also include a dashboard of the type disclosed in the aforementioned patent application. Still further, patient support apparatus 20 may be configured to issue any of the reminders in any of the manners disclosed in the aforementioned '638 patent application. Other types of control panels 48*a*, however, may alternatively be used.

Figure 10:
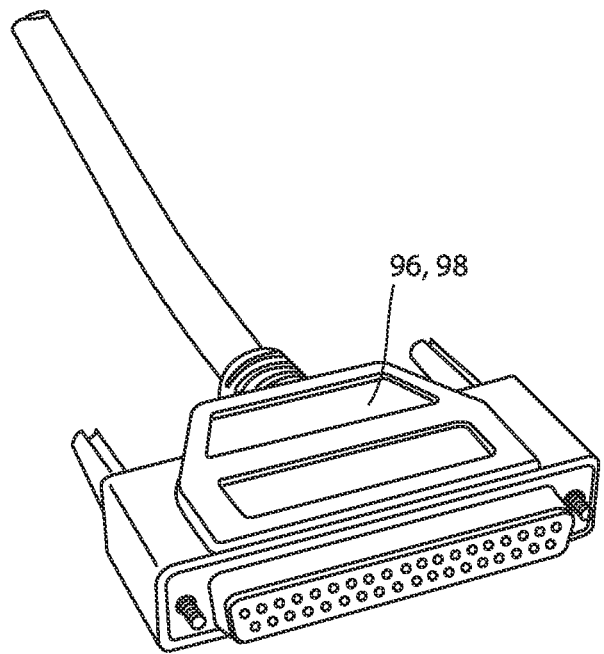
FIG. 10 is a perspective view of a prior art 37-pin female cable connector.

Communication sensor 120 (FIG. 6) is adapted to detect when cable interface 88 is in communication with wall outlet 60 via a cable 90. In one embodiment, communication sensor 120 detects the presence of a cable 90 connected between interface 88 and wall outlet 60 by monitoring the voltage, if any, on at least two pins 114*a* and 114*b* of cable interface 88. In some embodiments, the two pins are what is commonly referred to as the Nurse Call Plus (+) pin and what is commonly referred to as the Priority Normally Open/Normally Closed (NO/NC) pin. FIG. 10 illustrates a typical arrangement and identification of the pins for a common 37-pin connector. As can be seen therein, pin twenty-five corresponds to the Nurse Call Plus (+) pin, and pin thirty corresponds to the Priority Normally Open/Normally Closed pin. Accordingly, when communication sensor 120 is coupled to a cable interface 88 having the pin arrangement shown in FIG. 10, communication sensor 120 detects the voltage, if any, on both pins twenty-five and thirty, which correspond to pins 114a and 114b of FIG. 6. This voltage is generated by the nurse call system 68 and delivered to corresponding pins in wall outlet 60 (which in turn are delivered to pins 114a and 114b of interface 88 if a cable 90 is connected from wall outlet 60 to patient support apparatus 20.) If communication sensor 120 detects a voltage on one or both of these pins, it forwards a message to controller 112 indicating that a cable 90 is currently coupled between patient support apparatus 20 and wall outlet 60. If no voltage is detected on either of these pins, communication sensor 120 forwards a message to controller 112 indicating that no cable 90 is coupled between patient support apparatus 20 and wall outlet 60.

Communication sensor 120 monitors the voltage on the two pins 114a and 114b because it has been found that most manufacturers of nurse call systems 68 will generate a voltage on either or both of these pins of their respective wall outlet 60. Such voltage typically, although not necessarily always, ranges from about five to twenty-seven volts. Communication sensor 120, in at least one embodiment, is constructed to detect any voltage that is greater than about 0.3 volts (positive or negative), although it will be understood that this threshold detection level may be changed. If a voltage of about 0.3 volts or greater is detected on either pin 114a or pin 114b, or on both of them, communication sensor 120 concludes that a cable 90 is currently connected between patient support apparatus 20 and wall outlet 60 (and thus nurse call system 68), and sends a message to controller 112 indicating the existence of this wired connection, as mentioned. If no voltage of about 0.3 volts or greater is detected on either of pins 114a or 114b, communication sensor 120 concludes that no wired connection is present and forwards a message indicating such to controller 112.

In the embodiment shown in FIG. 6, patient support apparatus 20 is also configured to communicate with wall outlet 60 in a wireless manner (e.g. without cable 90). This can be seen from the presence of wireless interface 100 on patient support apparatus 20, and more specifically from the inclusion of radio frequency transceiver 136 within wireless interface 100. Wireless interface 100 also includes an infrared transceiver 128. As will be discussed in greater detail below, wireless interface 100 is used to establish a wireless communication link 58 with wall outlet 60 by wirelessly communicating with an adjacent headwall unit 94 that is coupled by a cable 90 to wall outlet 60.

FIG. 6 illustrates several internal components of headwall unit 94. These components includes cable interface 116, a controller 130, a communication sensor 132, a battery 134, an infrared (IR) transceiver 138, and a Bluetooth transceiver 140. IR transceiver 138 of wireless headwall unit 94 is adapted to communicate using infrared signals with IR transceiver 128 of patient support apparatus 20. Bluetooth transceiver 140 of wireless headwall unit 94 is adapted to communicate using Bluetooth communications with Bluetooth transceiver 136 of patient support apparatus 20.

Controller 130 communicates with communication sensor 132, transceivers 138 and 140, as well as with additional electronics that are present on headwall unit 94. The additional electronics may include any of the electronics disclosed in any of the following commonly assigned patent applications, and wireless headwall unit 94 may be configured to perform any of the functions disclosed in the following commonly assigned patent applications: Ser. No. 16/215,911 filed Dec. 11, 2018, by inventors Alexander Bodurka et al. and entitled HOSPITAL HEADWALL COMMUNICATION SYSTEM; Ser. No. 16/217,203 filed Dec. 12, 2018, by inventor Alexander Bodurka, and entitled SMART HOSPITAL HEADWALL SYSTEM; and Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosures of both of which are incorporated herein by reference.

Wireless headwall unit 94 is coupled to a wall outlet 60 by way of cable 90 having a connector 96 that is adapted to be inserted into wall outlet 60. As was noted, in some embodiments, such as wireless headwall unit 94a of FIG. 5, cable 90 may be omitted and wireless headwall unit 94a may be inserted directly into wall outlet 60 by way of a connector 102. Further, as was noted previously, although FIG. 6 illustrates both a cable 90 coupling patient support apparatus 20 to wall outlet 60 and a cable 90 extending from headwall unit 94 to a free end, a typical room (or bay of a room) in a healthcare facility will only include a single cable 90 that, depending upon the presence or absence of headwall unit 94, will extend between patient support apparatus 20 and wall outlet 60, or between headwall unit 94 and wall outlet 60. Thus, the two different cables 90 of FIG. 6 illustrate two different options for setting up communications between patient support apparatus 20 and wall outlet 60.

Cable interface 116 of headwall unit 94 (FIG. 6) communicates with cable 90 in the same manners as cable interface 88 of patient support apparatus 20. That is, the signals on the various pins of 114 of wall outlet 60 are communicated to controller 130 via cable 90 and cable interface 116, and controller 130 is adapted to forward those signals to wireless interface 100 of patient support apparatus 20 using transceivers 138 and/or 140. Likewise, wireless headwall unit 94 is adapted to receive data from patient support apparatus 20 via one or both of transceivers 138 and/or 140 and to forward the received data, as appropriate, to corresponding pins 114 of connector 98 of cable 90 (which are forwarded to wall outlet 60 when the opposite end (connector 96) of cable 90 is inserted in wall outlet 60).

Infrared transceiver 138 of headwall unit 94 acts as a location transceiver. Infrared transceiver 138 is a short range transceiver that emits a short range signal containing an identifier that is unique to that particular wireless headwall unit. Infrared transceiver 128 of patient support apparatus 20 is able to detect the short range signal from infrared transceiver 138 when the patient support apparatus 20 is positioned adjacent to headwall unit 94 (e.g. within approximately a meter or two). Patient support apparatus 20 forwards this unique signal to an off board server, such as server 78 and/or remote server 84, which contains a table correlating the unique identifiers of each headwall unit 94 to their location within the healthcare facility. This table is generated during a survey of the headwall units 94 when they are initially installed within the healthcare facility. Server 78 is therefore able to determine the location of each patient support apparatus 20 within the healthcare facility whenever the patient support apparatus 20 is positioned adjacent a headwall unit 94. Further explanation of one manner in which transceivers 128, 136, 138, and 140 may operate are provided in the following commonly assigned U.S. patent applications: Ser. No. 16/215,911 filed Dec. 11, 2018, by inventors Alexander Bodurka et al. and entitled HOSPITAL HEADWALL COMMUNICATION SYSTEM; Ser. No. 16/217,203 filed Dec. 12, 2018, by inventor Alexander Bodurka, and entitled SMART HOSPITAL HEADWALL SYSTEM; and Ser. No. 16/193,150 filed Nov. 16, 2018, by inventors Alexander Bodurka et al. and entitled PATIENT SUPPORT APPARATUSES WITH LOCATION/MOVEMENT DETECTION, the complete disclosures of all of which are incorporated herein by reference.

Bluetooth transceivers 136 and 140 are used by controllers 112 and 130, respectively, to transmit audio signals between patient support apparatus 20 and wireless headwall unit 94, such as, but not limited to, the audio signals used to convey the voice signals of the patient and the remotely positioned nurse. Such audio signals may also include the audio signals from television 86 and/or a radio or other entertainment device positioned in the room 70. Bluetooth transceivers 136 and 140 may also be used to transmit other data, such as, but not limited to, status data regarding the status of patient support apparatus 20, one or more messages indicating an exit detection alert has been issued, and/or other data. In some embodiments, wireless headwall unit 94 and patient support apparatus 20 are configured to exchange audio signals therebetween in any of the manners disclosed in commonly assigned U.S. patent application Ser. No. 62/833,943 filed Apr. 15, 2019, by inventors Alexander Bodurka et al. and entitled PATIENT SUPPORT APPARATUSES WITH NURSE CALL AUDIO MANAGEMENT, the complete disclosure of which is incorporated herein by reference.

In many embodiments, infrared transceivers 128 and 138 are used to initially establish the Bluetooth communication link between patient support apparatus 20. In such embodiments, transceivers 128 and 138 may exchange a unique patient support apparatus ID and a unique wireless headwall unit ID. These IDs are then used as addresses for the wireless communication between patient support apparatus 20 and wireless headwall unit 94. Such addresses ensure that patient support apparatus 20 only establishes a wireless communication link 58 with a headwall unit 94 that is positioned adjacent to the patient support apparatus 20, even when other wireless headwall units 94 may be within range of Bluetooth transceiver 136. In other words, patient support apparatus 20 only establishes a wireless communication link 58 with the headwall unit 94 that its IR transceiver 128 has linked to, and due to the IR transceiver's limited range, this only happens when patient support apparatus 20 is positioned adjacent to headwall unit 94. Still other ways of communicating between patient support apparatus 20 and wireless headwall unit 94 may be utilized.

Communication sensor 132 of wireless headwall unit 94 operates in the same manner as communication sensor 120 of patient support apparatus 20. That is, communication sensor 132 is electrically coupled to pins 114a and 114b (corresponding to the Nurse Call Plus (+) and Priority Normally Open/Normally Closed (NO/NC) pins) and checks to see if a voltage is detected on either or both of these pins. If it detects a voltage on either or both of these pins, it concludes that connector 98 of cable 90 is coupled to both interface 116 and wall outlet 60. If it does not detect a voltage on at least one of these pins, it concludes that no cable 90 is coupling interface 116 to wall outlet 60.

In at least one embodiment, controller 130 of wireless headwall unit 94 is configured to report the output of communication sensor 132 (i.e. whether interface 116 is coupled to wall outlet 60 by a cable 90 or not) to patient support apparatus 20. That is, controller 130 uses Bluetooth transceiver 140 (or IR transceiver 138, in some embodiments), to transmit a message to patient support apparatus 20 indicating whether headwall unit 94 is connected to wall outlet 60 or not. In at least one embodiment, patient support apparatus 20 includes an indicator that controller 112 illuminates, displays, or otherwise controls in order to indicate to the user the status of wireless headwall unit 94 vis-a-vis wall outlet 60. In such embodiments, controller 112 may be configured to illuminate an indicator in a first color (e.g. red or amber) if wireless headwall unit 94 transmits a message to patient support apparatus 20 indicating that it is not coupled to wall outlet 60 (as detected by communication sensor 132), and to illuminate the indicator in a second color (e.g. green) if wireless headwall unit 94 transmits a message to patient support apparatus 20 indicating that it is coupled to wall outlet 60 (as also detected by communication sensor 132). In this manner, patient support apparatus 20 provides an indication to the user thereon of the communication status of wireless headwall unit 94.

In some embodiments of patient support apparatus 20, it is configured to automatically select a wired or wireless communication method for communicating with wall outlet 60 based on the signals received from communication sensors 120 and 132. In such embodiments, if communication sensor 120 detects a voltage on pins 114a and/or 114b, controller 112 automatically communicates with wall outlet 60 using cable interface 88. On the other hand, if communication sensor 132 detects a voltage on pins 114a and/or 114b and controller 130 sends a message indicating this detection to patient support apparatus 20 (and to controller 112), controller 112 automatically communicates with wall outlet 60 by sending messages to headwall unit 94 using wireless interface 100. The communication may include not only the audio signals from the remote nurse and/or patient positioned on patient support apparatus 20, but also status data regarding patient support apparatus 20, such as, but not limited to, an alert status of exit detection system 56, the status of side rails 34 (e.g. raised or lowered), the status of a brake, the height of litter frame 28, and/or other status data.

In still other embodiments, controller 112 is configured to receive a message from headwall unit 94 indicating whether it should look for cable 90 (via communication sensor 120). Such a message may be received from headwall unit 94 when headwall unit 94 establishes that a cable 90 is present from itself to wall outlet 60. Thus, in such cases, controller 112 may disable its monitoring of the presence/absence of a cable that it would otherwise carry out using sensor 120. As will be discussed, the enablement/disablement of this monitoring feature may be a condition that is synced between patient support apparatus 20 and headwall unit 94 when the two first establish wireless communication link 58.

In at least one embodiment, controller 112 is configured, after automatically selecting a wired or wireless communication method (e.g. interface 88 or 100), to continue to use the automatically selected communication method until it either receives a signal from one of the communication sensors 120 or 132 indicating that the currently selected communication method is no longer viable (e.g. a voltage on pins 114a or 114b is no longer detected), it is instructed by a caregiver to switch communication methods, or it receives a message from headwall unit 94 indicating what communication method to use (or/or a message to disable/enable the monitoring of cable 90's presence). For example, if a caregiver unplugs a cable 90 from wall outlet 60 to patient support apparatus 20 and thereafter couples a cable 90 between wall outlet 60 and headwall unit 94, the former act will be detected by communication sensor 120 (if cable monitoring is enabled), while the latter act will be detected by communication sensor 132. Based on the signals received from these two sensors 120 and 132, controller 112 may automatically switch from wired communication via interface 88 to wireless communication via interface 100. Patient support apparatus 20 can therefore automatically select whichever communication method is available without requiring any manual instructions or manipulation of any controls on any of the control panels 48 by the caregiver. However, as noted above, Network transceiver 118 (FIG. 6) is a wireless transceiver adapted to communicate with one or more wireless access points 76 of the healthcare facility's local area network 74. In some embodiments, transceiver 118 may be a WiFi transceiver adapted to transmit and receive wireless electrical signals using any of the various WiFi protocols (IEEE 802.11b, 801.11g, 802.11n, 802.11ac . . . etc.). In other embodiments, network transceiver 118 may be a transceiver adapted to communicate using any of the frequencies, protocols, and/or standards disclosed in commonly assigned U.S. patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference. In still other embodiments, transceiver 118 may be a wired transceiver that communicates with network 74 over a wired network, such as an Ethernet cable or the like. Regardless of whether transceiver 118 is a wired or wireless transceiver, it enables controller 112 to communicate with one or more servers on the healthcare facility's network 72, such as, but not limited to, patient support apparatus server 78.

Controller 112 uses network transceiver 118 to send messages to server 78 (and/or server 84) indicating the status patient support apparatus 20, headwall unit 94, and/or other information. Suh status information includes data indicating whether patient support apparatus 20 is communicating via cable interface 88 or wireless interface 100, whether cable 90 is coupled between interface 88 and outlet 60, whether a cable is coupled between interface 116 and outlet 60, well as status data regarding battery 122 and/or 134, and other information. In some embodiments, server 78 and/or server 84 are configured to share this data with one or more other devices within the healthcare facility. For example, in at least one embodiment, server 78 and/or server 84 are configured to transmit the communication status of patient support apparatus 20 to one more electronic devices 142 (FIG. 4), such as the electronic devices 104a and/or 104b disclosed in commonly assigned U.S. patent application Ser. No. 62/868,947 filed Jun. 30, 2019, by inventors Thomas Durlach et al. and entitled CAREGIVER ASSISTANCE SYSTEM, the complete disclosure of which is incorporated herein by reference. The electronic devices 142 may be smart phones, tablet computers, laptop computers, desktop computers, and/or other computing devices that are in communication with network 74 and therefore able to receive data from patient support apparatus server 78.

Memory 144 may be comprised of any one or more of the following: non-volatile flash memory, Random Access Memory (RAM), Read Only Memory (ROM), a mechanical hard drive, a solid state hard drive, etc. Memory 144 may contain not only the instructions followed by controller 112 and the data used for carrying out those instructions, but also data defining the current status of one or more conditions, some of which may pertain to components onboard patient support apparatus 20 (e.g. exit detection system 56, siderails 354, etc.), and some of which may pertain to components off-board patient support apparatus 20 (e.g. room light 62a, reading light 62b, TV 86, nurse call system 68, and/or headwall unit 94). As will be discussed in greater detail below, the state values of some of these conditions are automatically synced with the state values of corresponding conditions that are present onboard headwall unit 94 when patient support apparatus 20 and headwall unit 94 first establish communications with each other.

FIG. 7 illustrates one example of a patient control panel 48c that may be incorporated into patient support apparatus 20 and positioned at a location on patient support apparatus 20 that is convenient for a patient to access while supported on support deck 30, such as on an interior side of one of the siderails 34. Control panel 48c includes a plurality of controls 126a-n that are intended to be operated by a patient. A nurse call control 126a, when pressed by the patient, sends a signal to the nurse call system 68 requesting that a remotely positioned nurse talk to the patient. A Fowler-up control 126b, when pressed by the patient, causes a motorized actuator onboard patient support apparatus 20 to raise Fowler section 40 upwardly. A Fowler-down control 126d, when pressed by the patient, causes the motorized actuator to lower Fowler section 40 downwardly. A gatch-up control 126c, when pressed by the patient, causes another motorized actuator to raise a knee section of support deck 30, while a gatch-down control 126e causes the motorized actuator to lower the knee section of support deck 30.

A volume-up control 126f, when pressed by the patient, causes patient support apparatus 20 to send a signal to an in-room television 86 instructing it to increase its volume, while a volume down control 126h, when pressed, causes patient support apparatus 20 to send a signal to the television 86 instructing it to decrease its volume. A channel-up control 126g, when pressed by the patient, causes patient support apparatus 20 to send a signal to the television 86 instructing it to increase the channel number, while a channel-down control 126i, when pressed, causes patient support apparatus 20 to send a signal to the television instructing it to decrease the channel number.

A mute control 126j, when pressed, causes patient support apparatus 20 to send a signal to the television instructing it to either mute itself or unmute itself, depending upon whether the television is currently muted or unmuted. In other words, mute control 126j is a toggle control that alternatingly sends mute and unmute commands to the television when it is pressed.

Power control 126k (FIG. 7) is a toggle control that, when pressed, sends a signal to the television to either turn on or turn off, depending upon the television's current power status. Closed-captioning control 126l is another toggle control that, when pressed, sends a signal to the television to either turn on its closed-captioning feature or to turn off its closed captioning feature, depending upon whether the closed-captioning feature is currently on or off.

Control 126m is a toggle control that, when pressed, sends a signal to a room light 62a to either turn on or turn off, depending upon the current state of the room light 62a. Control 126n is another toggle control that, when pressed, sends a signal to reading light 62b to either turn on or turn off, depending upon the current state of the reading lights 62b. Both of lights 62a and 62b are positioned off-board the patient support apparatus 20.

It will be understood that not only the number of controls 126 on control panel 48c (FIG. 7), but also the functions of the controls 126 on control panel 48c, the layout of the controls 126 on control panel 48c, and/or other aspects of control panel 48c may be modified from what is shown in FIG. 7. In some embodiments, control panel 48c is implemented on a pendant controller that includes a cable that is plugged into a port on patient support apparatus 20. Still other manners of implementing control panel 48c are also possible.

Patient support apparatus 20, in some embodiments, communicates various alerts and data through cable interface 88 to wall outlet 60 by changing the state of one or more relays, or their electrical equivalent, that are in communication with different pairs of the pins 114. Thus, for example, if an exit alert is detected by exit detection system 56, controller 112 may change a state of a first relay from being open to being closed, or vice versa, wherein that first relay is in electrical communication with a pair of pins 114 in cable interface 88. Similarly, if a patient presses a nurse call control (e.g. control 126a) indicating his/her request to speak with a remotely positioned nurse via nurse call system 68, controller 112 may change the state of another relay (from open to closed, or vice versa) that is in electrical communication with another pair of pins 114 in cable interface 88. The same opening or closing of a corresponding relay may also occur in response to the patient activating control 126m (FIG. 7) on patient support apparatus 20 for turning on/off a room light 62a, the patient activating control 126n on patient support apparatus 20 for turning on/off a reading light 62b, and/or the patient activating a control 126k on patient support apparatus 20 for turning on/off a television 86.

Headwall unit 94 (FIG. 6) may also contains a plurality of relays (not shown), or their electrical equivalent, that are in electrical communication with pairs of pins 114 in cable interface 116. During normal operation of headwall unit 94 (i.e. after the initial syncing process described herein is completed), controller 130 controls the states of these relays based on messages received from patient support apparatus 20 via IR transceiver 138 and/or RF transceiver 140. Thus, for example, if patient support apparatus 20 detects a patient exit and is configured to communicate that by closing a first relay that electrically couples together pins 30 and 31 (see FIG. 11) of cable interface 88, it will send an exit detection alert message to headwall unit 94 via one or more both of transceivers 138, 140, and controller 130 of headwall unit 94 will react by closing a first relay coupled to cable interface 116 that electrically couples together the same pair of pins 30 and 31.

A similar process happens for other events that occur on patient support apparatus 20, such as a nurse call being requested by the patient (control 126a), the reading light being turned on/off (control 126n), the room light being turned on/off (126m), and/or the TV being turned on/off (control 126k). That is, whenever one of these actions occurs on patient support apparatus 20, controller 112 sends a corresponding message to headwall unit 94 that causes controller 130 to open/close a relay inside headwall unit 94. The relay that is opened/closed by controller 130 changes the electrical state of a pair of pins in cable interface 116, and the particular pair of pins whose electrical state is changed by this opening/closing of a relay are the same pair of pins whose electrical state controller 112 changes in cable interface 88.

In addition to changing the states of various relays, controller 130 of headwall unit 94 also monitors the states (i.e. voltages) on various pins 114 of cable interface 116 and sends messages to patient support apparatus 20 via transceiver(s) 140, 138 that inform patient support apparatus 20 of the states of these pins. Thus, for example, headwall unit controller 130 monitors a first pin 114 (or pair of pins 114) that is/are associated with a nurse call light. The nurse call light, in some embodiments, controls a backlight for control 126a that, when activated, changes a state of a backlight positioned behind control 126a. Alternatively, or additionally, the nurse call light may be positioned elsewhere on control panel 48c (FIG. 7), or at other locations on patient support apparatus 20.

In some embodiments, the voltage across pins 25 and 28 (FIG. 11) is associated with the state of the nurse call light, and controller 130 monitors this voltage to see what state the nurse call system 68 is indicating that the nurse call light should be in (on/off). The nurse call light is illuminated (or has its illumination state, such as its color, changed) when the patient presses nurse call control 126a to request to speak with a remotely positioned nurse, and the nurse call system 68 acknowledges receipt of this casII. Notification of the activation of this control is sent to the nurse call system 68 via the opening/closing of a relay coupled to specific pins of wall outlet 60 (as discussed above), and the nurse call system 68, in response to successfully receiving this request, sends a signal back to the patient support apparatus 20 indicating that it should illuminate the nurse call light (or otherwise change its illumination state) as an acknowledgement by the nurse call system 68 that a call has been successfully placed. This response is communicated by changing the voltage across a pair of pins (e.g. pins 25 and 28 of FIG. 11). When controller 130 of headwall unit 94 detects a voltage across the nurse call request pins (25 and 28 of FIG. 11) of cable interface 116, it sends a message to patient support apparatus 20 (via transceivers 138 and/or 140) that causes controller 112 of patient support apparatus 20 to illuminate the nurse call light (or otherwise change its illumination state).

Controller 130 of headwall unit 94 (FIG. 6) also monitors the voltage between other pairs of pins 114 of cable interface 116 and reports, as appropriate, the state of this voltage to patient support apparatus 20 via one or both of transceivers 138, 140. One such other pair of pins are pins 114 associated with a nurse call answer light (see, e.g. pins 16 and 29 of FIG. 11). A nurse call answer light is a light that the nurse call system 68 instructs the patient support apparatus 20 illuminate (or have its illumination state changed) when a nurse actually answers the patient's call. Thus, the nurse call answer light differs from the nurse call light in that the former is illuminated when the nurse answers a call while the latter is illuminated when the nurse call system 68 acknowledges that the call was placed.

When patient support apparatus 20 is coupled to wall outlet 60 via a cable 90, controller 112 of patient support apparatus 20 performs the same type of monitoring of the pins 114 of cable interface 88 that controller 130 does with respect to cable interface 116. In such situations, controller 112 takes the same actions that it does when headwall unit 94 sends it a message informing it of a change in the state of a particular pair of pins. For example, controller 112 of patient support apparatus 20 may monitor the voltage across pins 24 and 28 (FIG. 11) to determine whether or not to illuminate its nurse call light, as well as to monitor the voltage across pins 16 and 29 to determine whether or not to illuminate its nurse call answer light. Controller 112 reacts to changes in voltage across these pins in the same manner as it reacts to a message from headwall unit 94 informing it of a similar change detected in the corresponding pins of cable interface 116. That is, controller 112 controls the illumination state of the nurse call light and/or the nurse call answer light in response to changes in the voltage across these pins.

It can therefore be seen that headwall unit 94 controls the voltages across various pins 114 in cable interface 116 (when patient support apparatus 20 is communicating wirelessly with wall outlet) in the same manner that patient support apparatus 20 controls the voltage across the corresponding pins 114 in cable interface 88 (when patient support apparatus 20 is communicating with wall outlet 60 via a cable 90). Similarly, headwall unit 94 monitors the voltage across various other pins 114 of cable interface 116 and sends messages to patient support apparatus 20 that cause patient support apparatus 20 to take the same actions that it would take in response to controller 112's detection of those same voltage changes on cable interface 88. Thus, cable interface 116 acts as a proxy for cable interface 88 when no cable is connected between patient support apparatus 20 and wall outlet 60.

FIG. 8 illustrates a table 150 in which are listed a plurality of conditions 152, a syncing direction 154, and examples of types of values 156 for the conditions 152. The conditions 152 identified in FIG. 8 correspond to various states that headwall unit 94 and/or patient support apparatus 20 may be in when they are initially paired together via wireless communication link 58. Because each device (patient support apparatus 20 and headwall unit 94) has its own copy of its current states for these conditions 152, and because the copy that each device has may not match the copy that the other device has when the devices are initially paired, both patient support apparatus 20 and headwall unit 94 are configured to executed a syncing process when they are initially paired. The syncing process matches a first subset of the conditions values that are present on the patient support apparatus 20 to those that are present on headwall unit 94 when they are first paired together, and matches other subset of the condition values that are present on headwall unit 94 to those that are present on headwall unit 94 when they are first paired together. By matching the values of some of patient support apparatus 20's conditions to headwall unit 94's condition values, and by matching the values of some of headwall unit 94's conditions to patient support apparatus 20's condition values, the syncing process ensures that, after initially being paired, both patient support apparatus 20 and headwall unit 94 are in agreement as to the current values for all of the conditions. Examples of several of these conditions and their various states will now be described in greater detail.

Some of the conditions that are synced between patient support apparatus 20 and headwall unit 94 when they first establish communications are the states of the relays present in each device (some of which were discussed above), while other conditions that are synced may refer to states that are not associated with relays. In either case, the current values for each condition may be stored in memories on each device.

During the initial syncing process, headwall unit 94 may have its relays in a first state while patient support apparatus 20 may have its relays in another state. When the headwall unit 94 and patient support apparatus 20 are first paired together, the question arises as to which relay state (that of the patient support apparatus's or that of the headwall unit's) is going to take precedence over the other. In other words, does patient support apparatus 20 change its relay states to match those of headwall unit 94, or does headwall unit 94 change its relay states to match those of patient support apparatus 20? Table 150 of FIG. 8 provides the answer to this question for each relay (as well as for multiple non-relay conditions that are synced between patient support apparatus 20 and headwall unit 94 in response to communication link 58 being established).

Specifically, column 154—the sync direction-indicates whether the patient support apparatus's state or the headwall unit's state will take priority over the other's state when they differ (if they don't differ, then the question of which one takes priority is moot). For each row in table 8 that states "bed_to_wall," this means that the patient support apparatus's current state of the condition listed in that row takes precedence over the headwall unit's current state of that condition when the two devices are synced together. Conversely, for each row in table 8 that states "wall_to_bed," this means that the headwall unit's current state of the condition listed in that row takes precedence over the patient support apparatus's current state of that condition when the two devices are synced together. This may be better understood with respect to several examples, which will now be described.

When patient support apparatus 20 and headwall unit 94 are first paired together, the relay inside of patient support apparatus 20 that controls the reading light 62b (condition 152a of FIG. 8) may be in a different state than the relay inside of headwall unit 94 that controls the reading light 62b. Thus, headwall unit 94 may, for example, be in a state where the reading light condition 152a has an off value (i.e. reading light 62b is turned off) and patient support apparatus 20 may be in a state where the reading light condition 152 has an on value (i.e. reading light 62b is turned on). When patient support apparatus 20 and headwall unit 94 are synced together, the state of reading lights 62b as set in patient support apparatus 20 takes precedence over the state of reading light 62b as set in headwall unit 94 (as indicated by column 154 of table 150 (FIG. 8). Thus, patient support apparatus 20 sends one or more messages to headwall unit 94 during the syncing process indicating its value of reading light condition 152a, and controller 130 of headwall unit 94 changes its value of reading light condition 152a to match that of the patient support apparatus's.

Similarly, if the states of the room light 62a (condition 152b of FIG. 8) differ between patient support apparatus 20 and headwall unit 94 when the two are initially paired together, the state of this condition 152b in patient support apparatus 20 takes precedence over the state of this condition in headwall unit 94. Patient support apparatus 20 sends one or more messages to headwall unit 94 during the syncing process indicating its current state of room light condition 152b, and controller 130 of headwall unit 94 changes its state of room light condition 152b to match that of the patient support apparatus's. In some embodiments, the state values of conditions 152a and 152b may correspond to voltages and/or open or closed states of relays associated with pins 2 and 3 (FIG. 11), although the values of these conditions 152a and/or 152b may be associated with other and/or additional pins 114.

As shown in FIG. 8, the state of conditions 152e, 152f, 152g, 152s, and 152v within patient support apparatus 20 all take precedence over the corresponding states of these conditions within headwall unit 94 during the syncing process. Controller 112 of patient support apparatus 20, as part of the syncing process, sends the current values for the states of these conditions to controller 130 of headwall unit 94, and controller 130 changes its corresponding state values for these conditions to match those received in the message(s) from patient support apparatus 20.

Condition 152e (FIG. 8) refers to the condition of nurse call request control 126a. If a patient has activated the nurse call control 126a, then the state value of condition 152e is set by patient support apparatus 20 to "on." If the patient has not activated the nurse call control 126a, then the state value of condition 152e is set by patient support apparatus 20 to "off." As was discussed previously, controller 112 may set the state of condition 152e to these two different values by controlling a relay associated with a specific pair of pins 114 of cable interface 88 (e.g. pins 25 and 26, FIG. 11) and/or by storing a corresponding value in memory 144.

Condition 152*f* (FIG. 8) refers to the condition of an exit detection alert (or other high priority alert) that takes place on patient support apparatus 20. If exit detection system 56 has detected a patient exit, then controller 112 sets the state value of condition 152*f* to "on." If exit detection system 56 has not detected a patient exit, then controller 112 sets the state value of condition 152*f* to "off." As was discussed previously, controller 112 may set the state of condition 152*f* to these two different values by controlling a relay associated with one or more pairs of pins 114 of cable interface 88 (e.g. pins 30 and 31, FIG. 11), and/or by storing a corresponding value in memory 144.

Condition 152*g* (FIG. 8) refers to the condition of television 86. If a patient has utilized control 126*k* to turn on television 86, then controller 112 sets the state value of condition 152*g* to "on." If the patient has utilized control 126*k* to turn off television 86 (or the patient has not utilized control 126*k* to turn on television 86), then controller 112 sets the state value of condition 152*g* to "off." As was discussed previously, controller 112 is able to control television 86 to match condition 152*g* by controlling a relay and/or voltage associated with pins 33 and/or 34 (FIG. 11).

Condition 152*s* and 152 *v* (FIG. 8) refers to conditions of patient support apparatus 20 that may not be associated with particular pins 114. Condition 152*s* refers to a request from patient support apparatus 20 to headwall unit 94 for a diagnostics report from headwall unit 94. If patient support apparatus 20 has this condition recorded in its memory 144 as being requested, it sets the value of this condition to "yes." If patient support apparatus 20 has this condition recorded in its memory 144 as not being requested, it sets the value of this condition to "no."

Condition 152*v* refers to the condition of an IR session ID. Whenever patient support apparatus 20 and headwall unit 94 are paired together, IR transceiver 128 and IR transceiver 138 assign an identifier to their communication session. Patient support apparatus 20 records this session ID in its memory and forwards it to headwall unit 94 during the syncing process. When controller 130 of headwall unit 94 receives it, it overwrites, or otherwise syncs, its IR session ID value with the one received from patient support apparatus 20 during the syncing process.

Headwall unit 94 is configured to have its values of all of the remaining conditions 152 shown in table 150 of FIG. 8 take precedence over the corresponding values of these conditions in patient support apparatus 20. That is, headwall unit 94's values of conditions 152*c*, 152*d*, 152*h*, 152*i*, 152*j*, 152*k*, 152*l*, 152*m*, 152*n*, 152*o*, 152*p*, 152*q*, 152*r*, 152*t*, and 152*u* all take precedence over patient support apparatus 20's values of these conditions during the syncing process. Each of these conditions will now be described in additional detail.

Condition 152*c* (FIG. 8) refers to the condition of the nurse answer light discussed above. If a remotely positioned nurse has answered a patient's call placed to the nurse call system 68, then condition 152*c* is in an on state. If the nurse call system 68 has indicated that a nurse has not answered a patient's call (or no such patient call has been placed), then condition 152*c* is in an off state. As was discussed previously, controller 130 of headwall unit 94 may determine the state of the nurse answer light by determining the state of one or more specific pins 114 of cable interface 116 (e.g. pins 16 and 29).

Condition 152*d* (FIG. 8) refers to the condition of the nurse call light discussed above. If the nurse call system 68 has acknowledged a patient call placed from patient support apparatus 20 (via control 126*a*), then condition 152*d* is in an on state. If the nurse call system 68 has not acknowledged a patient call (or no such patient call has been placed), then condition 152*d* is in an off state. As was discussed previously, controller 130 of headwall unit 94 may determine the state of the nurse call light by determining the state of one or more specific pins 114 of cable interface 116 (e.g. pins 25 and 28).

Conditions 152*h-r* and 152*t-u* (FIG. 8) refers to conditions of patient support apparatus 20 that may not be associated with particular pins 114. Values for these conditions 152 (as well as the previously discussed conditions 152) may be stored in a memory onboard patient support apparatus 20 (e.g. memory 144), as well as a memory onboard headwall unit 94 (not shown).

Condition 152*h* refers to a type of TV 86 that is positioned within the same room as headwall unit 94. The type, in some embodiments, refers to a brand of television, and patient support apparatus 20 and/or headwall unit 94 have built-in intelligence indicating the sequence of voltages, and/or other messages, necessary to send different commands to different types of televisions in order to effectuate the desired response. In other words, for example, some TV brands require a certain sequence of voltages to raise the channel number, while other TV brans may require a different sequence of voltages (and/or different voltage levels) to raise the channel number. The state value for condition 152*h* identifies the brand/type of TV 86 associated with headwall unit 94 so that the TV 86 can be properly controlled.

Condition 152*i* (FIG. 8) refers to the open or closed (e.g. on or off) state of a pair of pins 114 that are to be interlocked together (i.e. electrically shorted together) in order for certain brands and/or types of nurse call systems 68 coupled to wall outlet 60 to be able to detect the absence/presence of patient support apparatus 20. Condition 152*j* refers to the open or closed (e.g. on or off) state of another pair of pins 114 that are to be interlocked together for other (sometimes referred to as "standard") nurse call systems 68 coupled to wall outlet 60 to be able to detect the absence/presence of patient support apparatus 20. Condition 152*k* refers to the open or closed (e.g. on or off) state of another pair of pins 114 that are to be interlocked together in order for audio signals to be properly communicated to/from the nurse call system 68 to wall outlet 60. For some nurse call systems 68, the absence of a closed circuit between one or more pairs of these interlock pins causes the nurse call system 68 to issue a "cord-out" alert, which is a signal to one or more nurses that the patient support apparatus 20 and/or its cable 90 has become disconnected from wall outlet 60.

Condition 152*l* refers to an interlock forcing function (that may be on or off) wherein the patient support apparatus 20 and/or headwall unit 94 couple together one or more of the interlock pins 114 of conditions 152*i*, *j*, and/or k without waiting to detect any voltage between certain pins of outlet 60. In other words, when this function is turned on, patient support apparatus 20 or headwall unit 94 (whichever one is coupled to wall outlet 60 by a cable) will electrically short one or more of the interlock pins 114 without waiting to detect any signals from the nurse call system 68. When this function is turned off, patient support apparatus 20 or headwall unit 94 will not electrically short one or more of the interlock pins 114 until it detects certain voltages on one or more pins 114.

Condition 152*m* refers to the on/off state of a cable detection function carried out by patient support apparatus 20. As was discussed above, controller 112 of patient support apparatus 20 is configured, when condition 152*m* is in an on state, to monitor the outputs of communication sensor 120 to detect whether a cable 90 is plugged into interface 88, and to switch to using cable interface 88 to communicate with wall outlet 60 when a cable 90 is detected. When condition 152*m* is in an off state, controller 112 stops monitoring the communication sensor 120's outputs and/or does not automatically switch over to using cable interface 88 for communication with wall outlet 60 if a cable 90 is detected.

Condition 152*n* refers to the amplification level (e.g. dB) that headwall unit 94 applies to the audio signals it receives from wall outlet 60 (e.g. a nurse's voice signals from nurse call system 68) and/or the audio signals it transmits to nurse call system 68 (e.g. the patient's voice signals). Condition 152*o* refers to the type (e.g. brand) of nurse call system 68 that is coupled to the particular wall unit 60 in that particular room.

Condition 152*p* refers to the voltage levels that the nurse call system 68 applies to various of the pins 114 of wall outlet 60, and/or the voltage levels that headwall unit 94 and/or patient support apparatus 20 have to supply to cable interfaces 116, 88 in order for the nurse call system 68 to properly interpret the data being communicated to nurse call system 68.

Condition 152*q* refers to whether cable 90 is currently connected from headwall unit 94 to wall outlet 60 and, as was discussed above, may be determined by communication sensor 120. Condition 152*r* refers to whether or not headwall unit 94 has been configured yet or not. Headwall units 94, when initially installed within a particular healthcare facility, are configured to match the healthcare facility's usage of the different pins in wall outlet 60, as well as to know the correct voltage levels and/or other signals that are transmitted to wall outlet 60 so that proper communication can take place between patient support apparatus 20, nurse call system 68, TV 86, and lights 62*a* and 62*b*.

Condition 152*t* refers to whether or not headwall unit 94 has been synced with the currently paired patient support apparatus 20. And condition 152*u* refers to the current charge status of battery 134, which may be expressed with different values (e.g. a percentage of charge remaining; needs/doesn't need replacement; hi, medium, or low charge, etc.).

The syncing process carried out by patient support apparatus 20 and headwall unit 94 starts, in some embodiments, immediately after the two devices are paired together. The syncing process begins by one of the two devices (20 or 94) sending to the other device its current values of a first subset of the conditions 152 shown in FIG. 8. The recipient device then syncs it values of those conditions to the values that it received from the sending device. The recipient device then sends the original sending device its current values of a second and different subset of the conditions 152 shown in FIG. 8. The recipient of that message (i.e. the original sending device) then syncs its values of those conditions to the values that it received from the original recipient device. The devices are then synchronized.

The subsets of the values that are sent refer to those conditions of which the sending device's values take precedence over the receiving device's values. In other words, with respect to FIG. 8. the subset of values that patient support apparatus 20 sends to headwall unit 94 for syncing are those values associated with conditions 152*a*, 152*b*, 152*e*, 152*f*, 152*g*, 152*s*, and 152*v*. Patient support apparatus 20 sends these values to headwall unit 94 and headwall unit 94 syncs its values of these conditions so that they match what patient support apparatus 20 sent.

The subset of values that headwall unit 94 sends to patient support apparatus 20 for syncing are those values associated with the rest of the conditions shown table 150 of FIG. 8. Specifically, headwall unit 94 sends its values of conditions 152*c-d*, 152*h-r*, and 152*t-u* to patient support apparatus 20 during the syncing process and controller 112 of patient support apparatus 20 syncs its values of these conditions so that they match what headwall unit 94 sent. After each device has transmitted its subset of condition values to the other device, and both devices have indicated to each other that they have synced their condition values with the subset of values they received from the other device, the syncing process is completed.

The syncing process thereafter doesn't occur again until the communication link between patient support apparatus 20 and headwall unit 94 is terminated, and these two devices are paired together again. Thus, when a patient support apparatus 20 is moved from a first room to a second room, it will automatically sync itself with the first headwall interface 94 it pairs with in the first room (and that headwall unit 94 will also automatically sync itself with the patient support apparatus 20), and subsequently the patient support apparatus 20 will automatically sync itself with a second headwall interface 94 in the second room (which will also sync itself to the patient support apparatus 20 when the two pair together) when the patient support apparatus 20 is moved to that new room. Still further, if the patient support apparatus 20 is moved from the first headwall unit 94 to a different room that has no headwall unit 94, but instead has only a cable 90 coupled to wall outlet 60, the patient support apparatus 20 will use the last set of conditions values that it possessed when communicating with the headwall unit 94 for communicating with the wall outlet via cable 90.

It will be understood that various modification may be made to the syncing process disclosed herein. These modifications include, but are not limited to, syncing fewer conditions 152 than what is shown in FIG. 8, syncing more conditions 152 than what is shown in FIG. 8, and/or syncing different conditions 152 than what is shown in FIG. 8. In some embodiments, patient support apparatus 20 is further configured to store additional information about the current settings and/or preferences of the patient assigned to patient support apparatus 20. For example, in some embodiments, controller 112 of patient support apparatus 20 may record the current channel that a patient is watching on television 86 in a first room and then, if the patient support apparatus 20 is moved to a different room with a different television 86, automatically send a message to the different television 86 in the different room to turn to the channel the patient was watching in the previous room. Controller 112 of patient support apparatus 20, may also, or alternatively, be configured to store other patient preferences, such as channel volume, closed captioning, and/or other preferences, and automatically transfer them to a television 86 in a different room so that the television is automatically synced with the patient's preferences when the patient support apparatus 20 is moved to that room.

It will be understood by those skilled in the art that the use of the term "transceiver" throughout this specification is not intended to be limited to devices in which a transmitter and receiver are necessarily within the same housing, or share some circuitry. Instead, the term "transceiver" is used broadly herein to refer to both structures in which circuitry is shared between the transmitter and receiver, and transmitter-receivers in which the transmitter and receiver do not share circuitry and/or a common housing. Thus, the term "transceiver" refers to any device having a transmitter component and a receiver component, regardless of whether the two components are a common entity, separate entities, or have some overlap in their structures.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A headwall unit adapted to be mounted to a headwall of a room in a healthcare facility, the headwall unit comprising:
 a nurse call interface adapted to electrically couple to a wall outlet mounted in the headwall, the nurse call interface including a set of pins adapted to electrically couple to a plurality of conductors defined in the wall outlet when the nurse call interface is coupled to the wall outlet, each of the pins adapted to be in different electrical states;
 a first wireless transceiver adapted to wirelessly communicate with a second wireless transceiver positioned onboard a patient support apparatus when the patient support apparatus is positioned adjacent to the headwall unit;
 a controller adapted to use the first wireless transceiver to establish a communication link with the patient support apparatus, the controller further adapted to perform a syncing process in response to the communication link being initially established, the syncing process comprising:
  receiving a plurality of state values from the patient support apparatus, the plurality of state values corresponding to a current state of the patient support apparatus; and
  syncing the electrical states of a subset of the set of pins to match the state values received from the patient support apparatus;
 wherein the controller is further adapted, after completing the syncing process, to change an electrical state of at least one pin in the subset of the set of pins in response to receipt of a message from the patient support apparatus indicating a change to the current state of the patient support apparatus.

2. The headwall unit of claim 1 wherein a first one of the state values received from the patient support apparatus defines an on or off state of a reading light, the reading light being adapted to provide illumination to a patient on the patient support apparatus, and wherein a second one of the state values received from the patient support apparatus defines an on or off state of a room light, the room light being adapted to provide illumination to an entire room in which the headwall unit it positioned.

3. The headwall unit of claim 1 wherein a first one of the state values received from the patient support apparatus defines an on or off state of a nurse call request, the nurse call request being adapted to notify a nurse call system coupled to the wall outlet of a patient's desire to speak with a nurse.

4. The headwall unit of claim 1 wherein a first one of the state values received from the patient support apparatus defines an on or off state of a priority alert signal, the priority alert signal being adapted to notify a nurse call system of a priority event occurring on the patient support apparatus.

5. The headwall unit of claim 1 wherein a first one of the state values received from the patient support apparatus defines an on or off state of a television control signal, the television control signal being adapted to instruct a television to be turned on or off.

6. The headwall unit of claim 1 further comprising a third wireless transceiver adapted to wirelessly communicate with a fourth wireless transceiver positioned onboard the patient support apparatus when the patient support apparatus is positioned adjacent to the headwall unit, wherein the communication link is established when both the first wireless transceiver and the third wireless transceiver are in communication with the second and fourth wireless transceivers, respectively, onboard the patient support apparatus, and wherein the first wireless transceiver is a radio frequency transceiver and the third wireless transceiver is an infrared transceiver.

7. The headwall unit of claim 1 wherein the controller is further adapted to send a second plurality of state values to the patient support apparatus in response to the communication link being established, the second plurality of state values corresponding to a current electrical state of a second subset of the set of pins, the second subset different from the subset.

8. The headwall unit of claim 1 wherein the controller is further adapted to receive audio signals from the patient support apparatus via the first wireless transceiver, to forward the audio signals to at least one of the pins, to receive a configuration message via the first wireless transceiver, wherein the configuration message includes an identification of a first pair of the pins that must be electrically shorted together to avoid triggering a cord-out alert in a nurse call system coupled to the wall outlet, and to receive a new configuration message via the first wireless transceiver, wherein the new configuration message includes a new identification of a second pair of pins that must be electrically shorted together to avoid triggering the cord-out alert, wherein the second pair of pins is different from the first pair of pins.

9. The headwall unit of claim 1 wherein the controller is further adapted to receive an exit alert message from the patient support apparatus and to change an electrical state of at least one of the pins in response to receiving the exit alert message.

10. The headwall unit of claim 1 further comprising a memory in which is stored a unique identifier that uniquely identifies the headwall unit, wherein the controller is further adapted to forward the unique identifier to the patient support apparatus using the first wireless transceiver.

11. A patient support apparatus comprising:
 a support surface adapted to support a patient thereon;

a first wireless transceiver adapted to wirelessly communicate with a second wireless transceiver positioned onboard a headwall unit mounted to a headwall of room in a healthcare facility;

a controller adapted to use the first wireless transceiver to establish a communication link with the headwall unit, the controller further adapted to perform a syncing process in response to the communication link being initially established, the syncing process comprising:

receiving a plurality of headwall state values from the headwall unit, the plurality of headwall state value corresponding to a current state of the headwall unit; and syncing a plurality of patient support apparatus state values to match the headwall state values received from the headwall unit;

wherein the controller is further adapted, after completing the syncing process and in response to a change in a current state of the patient support apparatus, to transmit a message to the headwall unit instructing the headwall unit to change one of the plurality of headwall state values.

12. The patient support apparatus of claim 11 further comprising a nurse answer light adapted to be illuminated when a remotely positioned nurse answers a call from the patient, wherein a first one of the headwall state values defines an on or off state of the nurse answer light.

13. The patient support apparatus of claim 12 further comprising a nurse call light adapted to be illuminated when the patient calls a remotely positioned nurse, wherein a first one of the headwall state values defines an on or off state of the nurse call light.

14. The patient support apparatus of claim 12 further comprising a cable detector adapted to detect a presence of a cable connecting the patient support apparatus to a wall outlet defined in the headwall, wherein a first one of the headwall state values defines an enabled or disabled state of the cable detector.

15. The patient support apparatus of claim 13 further comprising a memory in which is stored at least one of the following:

a configuration setting of the headwall unit, wherein a first one of the headwall state values defines a configured state or an unconfigured state of the headwall unit;

a television setting of a television coupled to the headwall unit, wherein a first one of the headwall state values defines a type of the television; or a cable setting of a cable extending between the headwall unit and a wall outlet defined in the headwall, wherein a first one of the headwall state values defines a connected state or an unconnected state of the cable.

16. The patient support apparatus of claim 13 further comprising a memory in which is stored an interlock setting of a pair of pins of the headwall unit, wherein a first one of the headwall state values defines an electrically shorted state or unshorted state of the pair of pins.

17. The patient support apparatus of claim 13 further comprising a third wireless transceiver adapted to wirelessly communicate with a fourth wireless transceiver positioned onboard the headwall unit when the patient support apparatus is positioned adjacent to the headwall unit, wherein the communication link is established when both the first wireless transceiver and the third wireless transceiver are in communication with the second and fourth wireless transceivers, respectively, onboard the headwall unit, and wherein the first wireless transceiver is a radio frequency transceiver and the third wireless transceiver is an infrared transceiver.

18. The patient support apparatus of claim 13 wherein the controller is further adapted to send audio signals to the headwall unit via the first wireless transceiver that are to be forwarded by the headwall unit to a wall outlet integrated into the headwall.

19. The patient support apparatus of claim 13 further comprising an exit detection system adapted to detect a patient exit from the support surface, wherein the controller is further adapted to send an exit alert message to the headwall unit via the first wireless transceiver that is to be forwarded by the headwall unit to a wall outlet integrated into the headwall.

20. The patient support apparatus of claim 13 further comprising:

a memory in which is stored a first unique identifier that uniquely identifies the patient support apparatus; and a network transceiver adapted to communicate with a computer network of the healthcare facility;

wherein the controller is further adapted to receive a second unique identifier of the headwall unit from the headwall unit and to forward both the first and second unique identifiers to a server on the computer network via the network transceiver.

\* \* \* \* \*